US009033006B2

(12) United States Patent
Perazzo et al.

(10) Patent No.: US 9,033,006 B2
(45) Date of Patent: May 19, 2015

(54) ORAL SYRINGE PACKAGING SYSTEM FOR HOSPITAL PHARMACIES

(76) Inventors: Nicholas J. Perazzo, Rosedale, MD (US); Robert A. Rosen, Owings Mills, MD (US); John G. Grosskopf, Jr., Ellicott City, MD (US); Mark Bennett, Baltimore, MD (US); D. Bruce Cohen, Raleigh, NC (US); John M. Chopper, Pasadena, MD (US)

(*) Notice: Subject to any disclaimer, the term of this patent is extended or adjusted under 35 U.S.C. 154(b) by 818 days.

(21) Appl. No.: 13/236,577

(22) Filed: Sep. 19, 2011

(65) Prior Publication Data
US 2012/0241043 A1 Sep. 27, 2012

Related U.S. Application Data

(60) Provisional application No. 61/384,217, filed on Sep. 17, 2010, provisional application No. 61/494,677, filed on Jun. 8, 2011.

(51) Int. Cl.
| | |
|---|---|
| B65B 3/04 | (2006.01) |
| B65B 3/00 | (2006.01) |
| B65B 59/00 | (2006.01) |
| B65B 57/02 | (2006.01) |
| B65B 3/28 | (2006.01) |
| B65B 3/30 | (2006.01) |
| B65B 5/04 | (2006.01) |
| B65B 7/28 | (2006.01) |
| G06F 19/00 | (2011.01) |
| A61J 7/00 | (2006.01) |

(52) U.S. Cl.
CPC ............... *B65B 3/003* (2013.01); *B65B 3/006* (2013.01); *B65B 59/00* (2013.01); *B65B 57/02* (2013.01); *B65B 3/28* (2013.01); *B65B 3/30* (2013.01); *B65B 5/045* (2013.01); *B65B 7/28* (2013.01); *G06F 19/3462* (2013.01); *A61J 7/0053* (2013.01)

(58) Field of Classification Search
USPC ........... 141/2, 27, 329, 98; 700/231, 232, 236
See application file for complete search history.

(56) References Cited

U.S. PATENT DOCUMENTS

| | | | |
|---|---|---|---|
| 4,230,112 | A | 10/1980 | Smith |
| 4,628,969 | A | 12/1986 | Jurgens et al. |
| 4,703,781 | A | 11/1987 | Meyer et al. |
| 4,718,463 | A | 1/1988 | Jurgens et al. |
| 5,692,640 | A | 12/1997 | Caulfield |
| 5,884,457 | A | 3/1999 | Ortiz et al. |
| 6,877,530 | B2 | 4/2005 | Osborne |
| 6,976,349 | B2 | 12/2005 | Baldwin |
| 6,991,002 | B2 | 1/2006 | Osborne |
| 7,017,622 | B2 | 3/2006 | Osborne |
| 7,036,288 | B2 | 5/2006 | Vetter |
| 7,096,212 | B2 | 8/2006 | Tribble |
| 7,117,902 | B2 | 10/2006 | Osborne |
| 7,207,152 | B2 | 4/2007 | Baldwin |

(Continued)

*Primary Examiner* — Timothy L Maust
*Assistant Examiner* — Timothy P Kelly
(74) *Attorney, Agent, or Firm* — Ober, Kaler, Grimes & Shriver; Royal W. Craig

(57) ABSTRACT

A semi-automated system suitable for use in a hospital setting for filling patient-specific liquid prescriptions to be administered by oral syringes on a just-in-time basis. The system enables hospital pharmacists to simplify and streamline their task, increasing the number of prescriptions that can be filled in a day, improving patient safety and care by minimizing medication errors and the consequences that ensue.

12 Claims, 19 Drawing Sheets

(56) References Cited

U.S. PATENT DOCUMENTS

| | | |
|---|---|---|
| 7,240,699 B2 | 7/2007 | Osborne |
| 7,260,447 B2 | 8/2007 | Osborne |
| 7,343,943 B2 | 3/2008 | Khan |
| 7,392,638 B2 | 7/2008 | Baldwin |
| 7,610,110 B1 | 10/2009 | Johnston |
| 7,610,115 B2 | 10/2009 | Rob |
| 7,631,475 B2 | 12/2009 | Baldwin |
| 7,681,606 B2 | 3/2010 | Khan |
| 7,783,383 B2 * | 8/2010 | Eliuk et al. .......... 700/245 |
| 8,271,138 B2 * | 9/2012 | Eliuk et al. .......... 700/260 |
| 8,386,070 B2 * | 2/2013 | Eliuk et al. .......... 700/214 |
| 2009/0067973 A1 | 3/2009 | Eliuk |
| 2010/0017031 A1 | 1/2010 | Rob |

* cited by examiner

ORAL SYRINGE PACKAGING SYSTEM FOR HOSPITAL PHARMACIES

CROSS-REFERENCE TO RELATED APPLICATIONS

The present application claims priority to U.S. provisional patent application Ser. No. 61/384,217 filed Sep. 17, 2010 which is incorporated herein by reference; and to U.S. provisional patent application Ser. No. 61/494,677 filed Jun. 8, 2011 which is also incorporated herein by reference.

BACKGROUND OF THE INVENTION

1. Field of the Invention

The present invention relates generally to oral syringe packaging equipment and more specifically to a partially automated system for preparing patient-specific doses of selected pharmaceutical liquid medication for administration by oral syringe on a just-in-time basis, for use in a hospital pharmacy.

2. Description of the Background

Oral syringes are well known instruments in the medical fields and are used to administer liquid medicine into the mouth, as an alternative to pills which can present a choking hazard or be expectorated, typically for infants/children and uncooperative or geriatric adults. The oral syringe directs liquid medicine to the back of the throat prompting a swallowing response. Injectable syringes, on the other hand, are used to administer medication into the body by injecting its contents through the skin. Injectable syringes utilize a needle on the tip of the syringe. Injectable syringes must be manufactured and packaged in a sterile environment. Research has shown that the potential for adverse drug events within the pediatric inpatient population is about three times as high as among hospitalized adults. See, Joint Commission, Preventing Pediatric Medication Errors, Issue 39 (2008). According to the Commission Report, the most common types of harmful pediatric medication errors were improper dose/quantity (37.5 percent) and unauthorized/wrong drug (13.7 percent), followed by improper preparation or dosage form. Oral syringes help to minimize these problems and are considered the gold standard for delivering medicine to children.

Oral syringes are comprised of a simple piston pump with a plunger that fits tightly in one end of a cylindrical tube (the barrel) and can be pushed or pulled along inside the barrel to create negative or positive relative pressure within the barrel that causes the syringe to take in or expel a liquid or gas through an orifice (nozzle) at the opposing end of the barrel. The barrel of an oral syringe is typically made of plastic and is at least partially transparent along its length with graduated markings to indicate the volume of fluid in the syringe based on the position of the plunger visible within the barrel. Oral syringes come in a wide range of sizes and with some variation in configuration. For example, some oral syringes have the nozzle located along the central axis while others have the nozzle offset from the central axis this variability makes it difficult to automate the filling process. Oral syringes are commonly marked in units of milliliters and come in standard sizes ranging from 0.5 to 60 milliliters. An annular flange partially or fully encircling the outside surface of the barrel is typically provided to facilitate compression of the plunger into the barrel. The plunger is also typically plastic as this provides a good seal within the barrel and is inexpensive to produce so as to be disposable, reducing the risk of contamination or transmission of communicable disease.

Pharmacies at in-patient medical facilities and other medical institutions fill a large number of prescriptions on a daily basis including prescriptions for liquid or compounded suspension medicines to be administered by oral syringe, and must do so accurately for medical safety reasons. The volume of an oral pediatric prescription's dose is determined by the child's weight. This makes it impractical to stock pre-filled syringes due to the wide range of fill volumes required. As a result, pediatric oral liquid doses are prepared in the hospital pharmacy on a patient-specific, just-in-time basis. The process of filling numerous, variously sized single dose prescriptions for delivery by oral syringe is time consuming, labor intensive and prone to human error. To insure that the medication is packaged error-free, the pharmacy technician must make sure that: (1) the syringe contains the correct medication; (2) the syringe contains the correct amount of medication; (3) the syringe is capped correctly; (4) the medication has not expired; (5) the medication has not been recalled; (6) the medication, when required, is shaken; (7) the medication, when required, has been properly refrigerated; (8) the medication, when required, has been properly protected from exposure to light; (9) the information on the syringe label is correct; (10) the syringe is placed into the correct bag; (11) the information on the bag containing the syringe is correct; (12) the bag is properly sealed; and (13) the syringe is protected from cross contamination from other medications. The process typically requires a pharmacist or pharmacy technician to retrieve the correct medication from a storage cabinet or refrigerated storage area. The liquid medications are typically stored in a container sealed with a safety cap or seal. After confirming the contents of the retrieved container and shaking the medication (if necessary), the technician manually opens the cap and inserts the tip of an oral syringe into the container, withdrawing the plunger to draw the medication into the barrel of the syringe. After filling with a proper amount, the tip of the syringe is covered with a cap for transport to the patient and the syringe is labeled to indicate its content, the intended recipient, and then bagged. Prior to administering the dose, the nurse can determine the amount of the dose by observing where the tip of the plunger or piston is located in the barrel. Oral syringes are relatively inexpensive and disposable.

Currently, the degree of automation in the hospital pharmacy for the packaging of oral syringes is very limited. Islands of automation exist, such as automatic labeling of the syringe and bagging of the filled and capped syringe. However, the filling and capping are done manually. Scanners, cameras, bar code readers and track-and-trace technology have not been applied on an integrated, comprehensive basis for the packaging of oral syringes in the hospital pharmacy. The potential to reduce medication errors using this technology is significant. Automated systems have been developed by Baxa, Inc., For Health Technologies, Inc., Intelligent Hospital Systems and others for the automated filling of injectable syringes.

For example, U.S. Pat. Nos. 6,991,002; 7,017,622; 7,631,475 and 6,976,349 are all drawn to automated removal of a tip cap from an empty syringe, placing the tip cap at a remote location, and replacing the tip cap on a filled syringe. U.S. Pat. Nos. 7,117,902 and 7,240,699 are drawn to automated transfer of a drug vial from storage to a fill station. U.S. Pat. No. 5,884,457 shows a method and apparatus for filling syringes using a pump connected by hose to a fluid source. U.S. Pat. No. 7,610,115 and Application 20100017031 show an Automated Pharmacy Admixture System (APAS). U.S. Application 20090067973 shows a gripper device for handling syringes of different diameters with tapered or angled gripper fingers. U.S. Pat. No. 7,343,943 shows a medication dose under-fill detection system. U.S. Pat. No. 7,260,447 shows an automated system for fulfilling pharmaceutical prescriptions. U.S. Pat. No. 7,681,606 shows an automated system and process for filling syringes of multiple sizes. U.S. Pat. No. 6,877,530 shows an automated means for withdrawing a syringe plunger. U.S. Pat. No. 5,692,640 shows a system for establishing and maintaining the identity of medication in a vial using preprinted, pressure sensitive, syringe labels.

The foregoing reference machines for packaging injectable syringes. The packaging process required for injectable syringes is significantly different than that for oral syringes. Injectable syringes must be packaged in a sterile environment as the medication is injected into the body. This requirement adds cost and complexity to the machine. Injectable medications, when packaged on a just-in-time basis as with the Baxa, For Health Technologies, and Intelligent Hospital System machines, must typically be prepared by the machine before the medication is filled into the syringe. The medication preparation process involves diluting the medication or reconstituting the medication from a powdered state with water. This process adds expense and slows down the packaging process as well. The Intelligent Hospital Systems syringe packaging system is designed to be used to package cytotoxic medications which are hazardous. To avoid harm to the operator, this machine uses a robot located within an isolating barrier at considerable cost. The Baxa, For Health Technologies, and Intelligent Hospital System machines require the use of expensive disposable product contact parts when a different medication is to be filled. The foregoing machines are not suitable for packaging oral syringes due to their capital cost, complexity, slow production rates, inability to handle oral medication containers, and the requirement of expensive disposable contact parts. Consequently, existing automation does not address the needs of medical institutions desiring an affordable pharmacy automation system for patient safety, prescription tracking and improved productivity. The present invention was developed to fill this void.

Oral syringes are manufactured in a variety of sizes with differing tip and plunger configurations. Moreover, oral medications are commonly provided in bulk form in variously sized bottles or containers having threaded screw caps that must be removed and replaced between uses. Additionally, in-patient medical facilities such as hospitals are moving toward electronic prescription ("e-prescription") systems which use computer systems to create, modify, review, and/or transmit medication prescriptions from the healthcare provider to the pharmacy. While e-prescribing improves patient safety and saves money by eliminating the inefficiencies and inaccuracies of the manual, handwritten prescription process, any syringe fill automation system suitable for use in a hospital setting must interface with an existing e-prescription system (which records and transmits prescriptions to the pharmacy), and must be capable of filling prescription orders in a just-in-time environment.

Given the diversity of oral syringes and medicines available, any semi-automated (or fully-automated) system will need sufficient dexterity to manipulate all the myriad prescription bottles containing the pharmaceuticals to be dispensed as well as variously sized oral syringes, bringing them together in a controlled environment to quickly and accurately fill and label each syringe and to verify its work as it proceeds in order to avoid errors in the process. Such a system would need to be reliably constructed so as to minimize downtime, quickly take and fill orders, be easy to clean and capable of maintaining an environment free from cross contamination. Such a system would also need to be able to interact with a human operator at multiple points in the operation.

The present inventors herein provide a semi-automated system suitable for use in a hospital setting for filling patient-specific doses of liquid medications to be administered by oral syringes on a just-in-time basis, as well as an automated alternative. The system enables hospital pharmacists to simplify and streamline their task, increasing the number of prescriptions that can be filled in a day, improving patient safety and care by minimizing medication errors and the consequences that ensue.

BRIEF DESCRIPTION OF THE DRAWINGS

The objects, features, and advantages of the present invention will become apparent from the following detailed description of the preferred embodiments and certain modifications thereof when taken together with the accompanying drawings in which like numbers represent like items throughout and in which.

DETAILED DESCRIPTION OF THE PREFERRED EMBODIMENT

Figure 1:
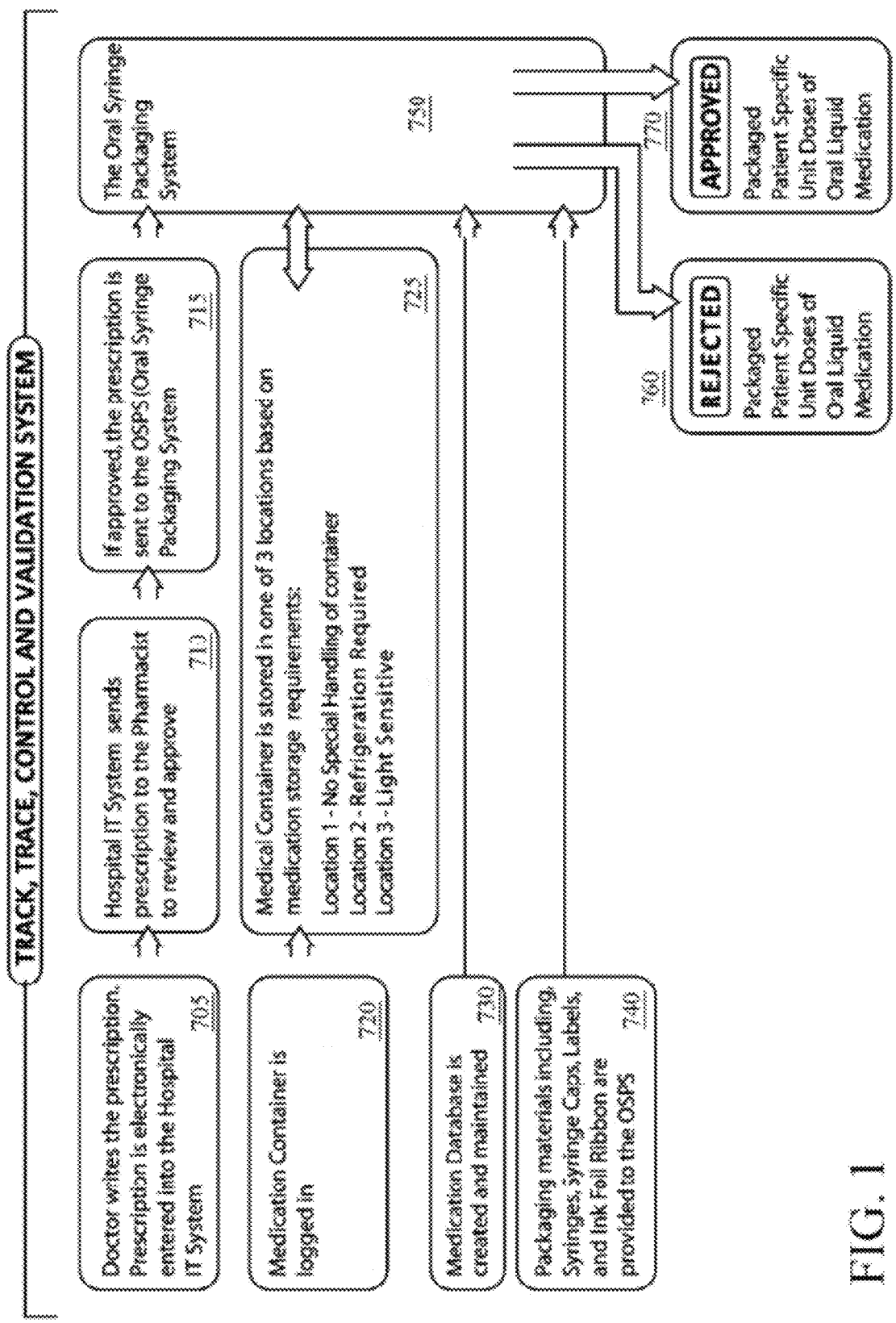
FIG. 1 is a flow chart of the overall method of the invention.

For the purposes of promoting an understanding of the principles of the invention, reference will now be made to the exemplary embodiment illustrated in the drawings and described below. The embodiment disclosed is not intended to be exhaustive or limit the invention to the precise form disclosed in the following detailed description. Rather, the embodiment is chosen and described so that others skilled in the art may utilize its teachings. It will be understood that no limitation of the scope of the invention is thereby intended. The invention includes any alterations and modifications in the illustrated device, the methods of operation, and further applications of the principles of the invention which would normally occur to one skilled in the art to which the invention relates.

The present invention includes both the system hardware as well as the process for preparing and tracking prescriptions of oral syringes by a series of integrated manual and automated steps with respect to preparing the syringe and the bulk medicine, and subsequently bringing the series together for filling the former from the latter. The invention relies on a conventional network architecture which includes a local OSPS (Oral Syringe Packaging System) computer. The OSPS computer is interfaced to a hospital host computer and receives oral syringe prescription instructions there from. In the majority of circumstances physicians submit prescriptions for oral syringes electronically to the hospital host computer and these prescriptions are communicated to the OSPS computer for fulfillment. The interface serves to parse/extract those oral medication prescriptions from all prescriptions submitted.

The local OSPS computer is programmed to know what must occur at each station and monitors to ensure that each step of the process is completed satisfactorily and that all decision rules are complied with. The local OSPS computer software implements a Medication Container Orientation and Log-In Process for semi-automated preparation and storage of bulk medicine containers to be used in filling and packaging oral syringes, and a Batch Fulfillment Process for semi-automated filling and packaging of oral syringes using the stored bulk medicine containers. In general terms, the semi-automated Medication Container Orientation and Log-In Process comprises the following steps:

a. Pharmacy technician (operator) removes the manufacturer's cap from bulk medicine container received from the pharmaceutical manufacturer and replaces the cap with an adapter cap (described below);
c. Software guides operator to scan the manufacturer's barcode label;
d. Software automatically prints a new unique adapter cap 2D barcode label and that label is attached to the adapter cap (as an alternative, the adapter cap can be provided with a pre-printed barcode label);
f. Software guides operator to rescan the manufacturer's barcode on the container label and the 2D barcode on the adapter cap;
g. If scanning checks, software guides operator to place medication container in a particular (logged) storage facility location.

The semi-automated Batch Fulfillment Process comprises the following steps:

a. Software guides operator to retrieve medication container from particular (logged) storage facility location;
b. Operator loads medication container into system;
c. 2D barcode on the adapter cap is scanned to make sure that all medication issues relating to that medicine container have been addressed, including refrigeration, expiration and light-sensitive storage;
d. Software guides operator to pick a syringe;
e. Software automatically prints label for the syringe;
f. The label is rescanned to ensure that the information is correct;
g. Operator places the syringe in the fixture at the syringe labeling station where the pre-printed label is attached to the syringe;
h. Operator scans the 2D barcode on the syringe at the fill/cap station.
i. Operator positions the syringe at the fill/cap station;
j. System/software automatically fills the syringe from medicine in medication container and caps the syringe;
k. Operator scans the syringe at the volume/weight check station;
l. System/software automatically inspects the syringe for proper weight or volume;
m. System/software automatically prints bag that the syringe will be packaged in;
n. Software automatically scans the printing on the bag to make sure that it is correct;
o. Operator places the syringe in the bag at the bagging station, and the system confirms that the syringe was placed in the bag, and seals the bag with the syringe in it.

All medication containers and medicines in those containers that have been logged in, each size syringe, each size adapter cap, syringe labels, bags, ink cartridges, etc. are automatically inventoried. As an item is used or consumed, an accounting of the amount of that item remaining is maintained. Track, Trace and Validation software monitors the entire process from the prescription approval by the pharmacist, log-in of the medication container through each step of the packaging process.

FIG. 1 is a more detailed flow chart of the overall method of the invention. The following method steps are performed semi-automatically with some manual intervention by or interaction with an operator for filling patient-specific oral syringes on a just-in-time basis. Note that "semi-automatic" necessarily entails manual intervention/interaction which has a propensity for introducing mistakes. The present method and apparatus is specifically designed to avoid mistakes and maintains comprehensive track-and-trace validation of each manual step:

At step 705 a physician writes an oral medicine prescription which is electronically entered into existing hospital host computer (as all prescriptions are so logged).

At step 710 the existing hospital host computer communicates the oral medicine prescription to the hospital pharmacy for approval. A pharmacist will typically review it.

If approved, then at step 715 the prescription is transmitted the local computer of the OSPS (Oral Syringe Packaging System) of the present invention. The oral syringe prescription is added to a batch fulfillment queue at the local OSPS computer. As described below the queue is multi-sorted so that all prescriptions for a particular type of medicine (e.g., Acetaminophen, cough syrup, etc.) can be fulfilled together, and at periods throughout the day an operator may run a batch fulfillment queue (typically batches are run a few times each day).

At commencement of batch fulfillment, the OSPS system preferably guides the operator in retrieving the appropriate medication container from OSPS storage (as will be described). Such guidance presupposes that a library of medicine containers is maintained and that each such medicine container be logged into the OSPS system so that its location and contents are known to the local OSPS computer. Consequently, as a precursor to batch fulfillment each new medication container is logged into OSPS storage by a barcode, RFID scan or similar identification scan (e.g., of the manufacturer's barcode). The manufacturer-applied cap must also be replaced by an adapter cap (to be described) which is separately labeled. All this occurs at step 720.

At step 725 based on the medication container login, the OSPS system guides the operator in properly storing the new medication container. The OSPS system (as described below) includes separate storage locations for three types of medication containers: Location 1—No Special Handling of container; Location 2—Refrigeration Required; Location 3—Light Sensitive medication container. Each storage compartment within each location may be enclosed by a magnetically-actuatable door so that access to each location may be electronically controlled by the local OSPS computer. Alternately, each storage compartment within each location may be illuminated by an LED light, so that access to the proper location may be electronically guided by illumination of the proper LED. As another alternative, each storage compartment within each location may be equipped with a light curtain so that the local OSPS computer can monitor access to the proper location. All these and other suitable forms of user-guidance/selection are considered to be within the scope and spirit of the present invention. In all such cases, the end result is an OSPS storage library of different oral medicines in their bulk containers, each properly logged in and stored in its corresponding storage location 1-3.

Similarly, at step 740 an inventory of packaging materials is maintained, including empty syringes in an array of sizes, syringe caps, labels (for barcodes), and ink foil printer ribbon.

In support of the OSPS system, at step 730 a comprehensive medication database is maintained at the OSPS computer.

The OSPS medication database includes the following:
1. Medication Information.
   a. Medication name
   b. Manufacturers barcode number
   c. Written information that corresponds to manufacturer's barcode number
   d. Whether medication needs to be shaken, if so the frequency and duration between fills
   e. Whether the medication needs to be refrigerated, if so refrigeration policy required
   f. Whether the medication is light sensitive, if so light sensitive protection required
2. Product information (pertaining to the individualized medication containers logged in).
   a. The OSPS 2D barcode number assigned to that specific container
   b. Fill size of that container in cc's
   c. Current amount of product remaining in that container after deducting for previous fills extracted by the syringes.
   d. Manufacturer's Expiration Date
   e. Date the medication container is logged-in at the Medication Container Log-In Orientation System.
   f. Pharmacy Policy Expiration Date: Container open date plus number of days before container expires (determined by pharmacist).
   g. Effective Expiration Date. This is the soonest of the manufacturer's expiration date or the date that the container is open plus the number of days that the open container will expire. (Pharmacy Policy Expiration Date).

Given all of the foregoing, at step 750 an operator may at any convenient time commence the batch fulfillment process. The more detailed substeps of the batch fulfillment process 750 are illustrated in the block diagram of FIG. 3.

After each oral syringe has been filled and package during batch fulfillment 750, it is inspected and either rejected at step 760 or approved at step 770.

The above-described method is herein implemented in several detailed embodiments of a system suitable for preparing patient-specific oral syringe doses. Various alternate embodiments of the invention may omit selected steps (and their performance station) where such is/are not required. The needs of the operating institution and the cost aspect of automating certain steps may direct which steps/stations (if any) are to be performed manually by an operator interfacing with the apparatus and which may be automated. A presently-preferred embodiment is described below with reference to FIG. 2.

Figure 2:
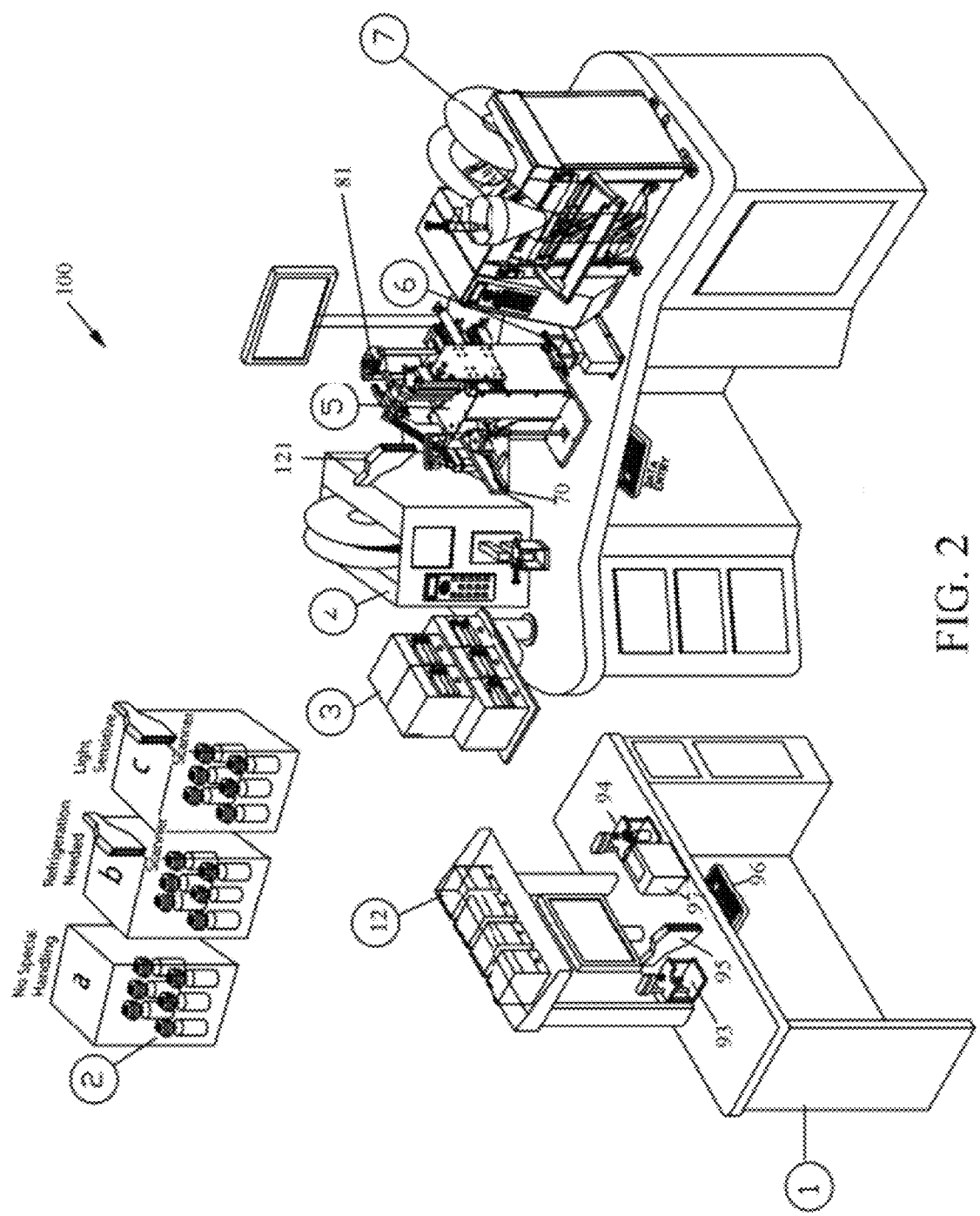
FIG. 2 is a perspective view of the entire pharmacy automation system 100 according to an embodiment of the invention.

As seen in FIG. 2, the pharmacy automation system 100 for packaging oral syringes generally comprises a standalone Medication Container Login & Orientation Station 1, with an included array of adapter cap storage bins 12. In addition, a proximate or remote Storage Facility 2 is provided for storing all logged in medication containers, with separate locations for the three types of medication containers: (a) Location 1—No Special Handling of container; (b) Location 2—Refrigeration Required; (c) Location 3—Light Sensitive medication container.

A storage bin 3 is provided for storage of empty syringes, and a syringe label printer and labeler station 4 is provided next. This is followed by a syringe fill/cap station 5, then a check weight and/or volume station 6, and lastly a bag printing and sealing station 7. The purpose and function of each of the foregoing stations 1-7 will become clearer in the context of a description of the Medication Container Orientation and Log-In Process (step 720), and Batch Fulfillment Process 750.

Medication Container Orientation and Log-In Process (step 720)

The OSPS system guides the operator in properly equipping and storing each bulk medication container.

Figure 4:
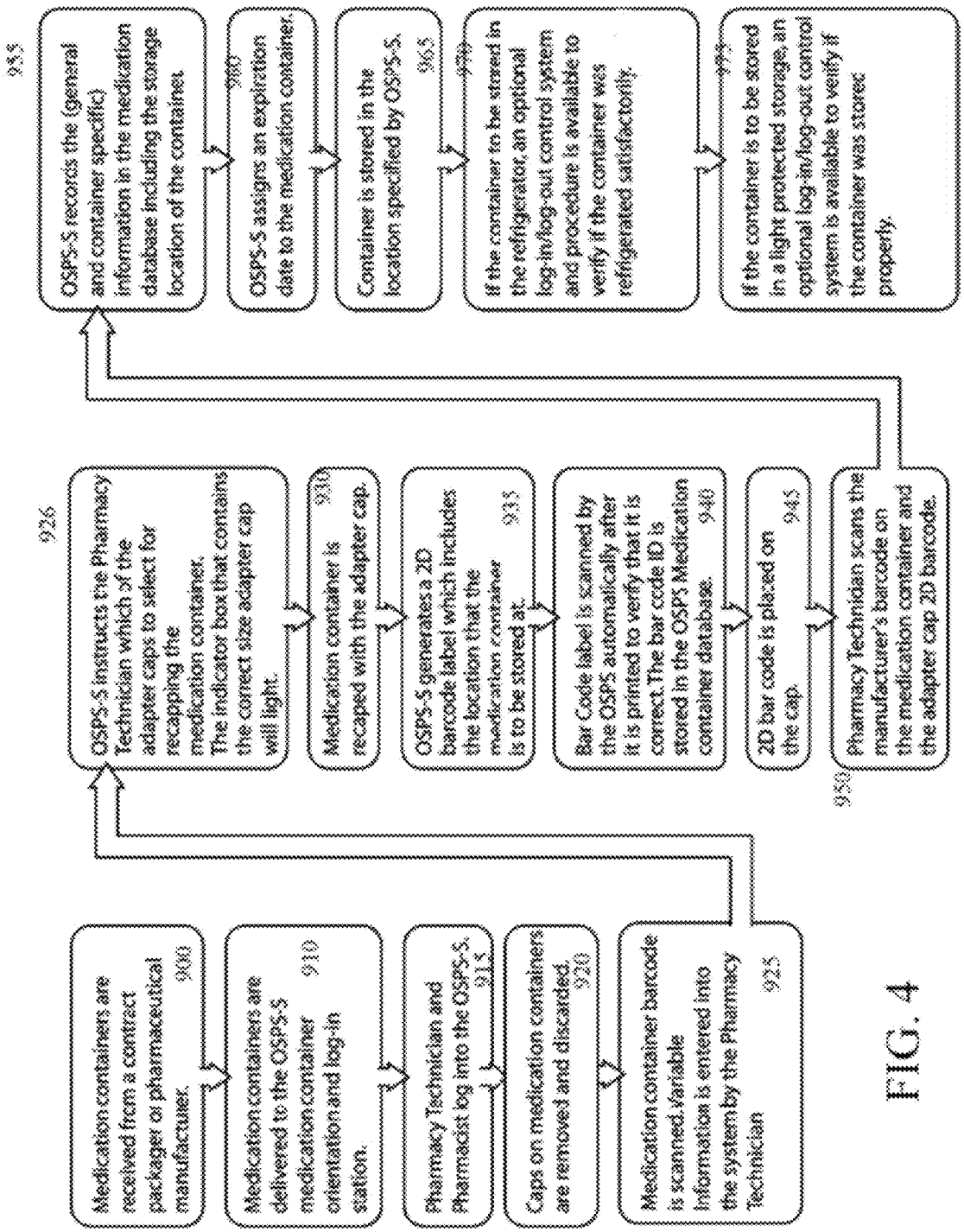
FIG. 4 is a more detailed block diagram of the medication container orientation and log-in process 720 of FIG. 1.

As shown in FIG. 4, at step 900, medication containers are received from a contract packager or pharmaceutical manufacturer.

At step 910, medication containers are delivered to the OSPS Medication Container Login & Orientation Station 1 (FIG. 2).

At step 915 the pharmacist and operator logs into the local OSPS computer.

At step 920 caps on medication containers are manually removed and discarded.

At step 925 the manufacturer-provided medication container barcode is scanned. Variable information is entered into the system by the pharmacy technician At step 926, the OSPS local computer instructs the operator which of the adapter caps to select for recapping the medication container. As above, each adapter cap storage compartment 12 may be enclosed by a magnetically-actuable door so that access to each location may be electronically controlled by the local OSPS computer, or illuminated by an LED light, or equipped with a light curtain so that the local OSPS computer can monitor access to the proper location. All these and other suitable forms of user-guidance/selection are considered to be within the scope and spirit of the present invention.

At step 930, the medication container is recapped with the adapter cap.

At step 935, the labeler shown at the Medication Container Login & Orientation Station 1 generates a 2D barcode label which includes the location that the medication container is to be stored at. The 2D bar code is placed on the adapter cap at step 945.

At step 940, the bar code label is automatically inspected immediately after printing to verify that its contents are correct and the bar code ID is stored in the OSPS database.

At step 950, the 2D bar code placed on the adapter cap and the pharmaceutical manufacturer's barcode are scanned using a scanner resident at the Medication Container Login & Orientation Station 1.

At step 955 all general and container specific information is recorded in the local OSPS computer database, including the storage location of the bulk container.

At step 960, the OSPS local computer assigns an expiration date to the medication container.

At step 965, the operator manually stores the container in the location specified by the OSPS local computer. If the container is to be stored in light protected storage 2(*c*), an optional log-in/log-out control system may be used to verify if the container was stored properly. This way, if the container is outside of the light protected storage area more than a specific number of minutes the OSPS local computer will not permit the syringe to be filled from that container.

At step 970 if the container is to be stored in the refrigerator, an optional log-in/log-out control system and procedure is available to verify if the container was refrigerated satisfactorily. This way, if the container is outside of the refrigerated storage area more than a specific number of minutes the OSPS local computer will not permit the syringe to be filled from that container, and will alert the Pharmacy Technician to remove and discard that container.

At step 975 if the container is to be stored in a light protected storage area, an optional log-in/log-out control system and procedure is available to verify if the container was stored appropriately. This way, if the container is outside of the light protected storage area more than a specific number of minutes the OSPS local computer will not permit the syringe to be filled from that container, and will alert the Pharmacy Technician to remove and discard that container.

Batch Fulfillment Process 750

Figure 3:
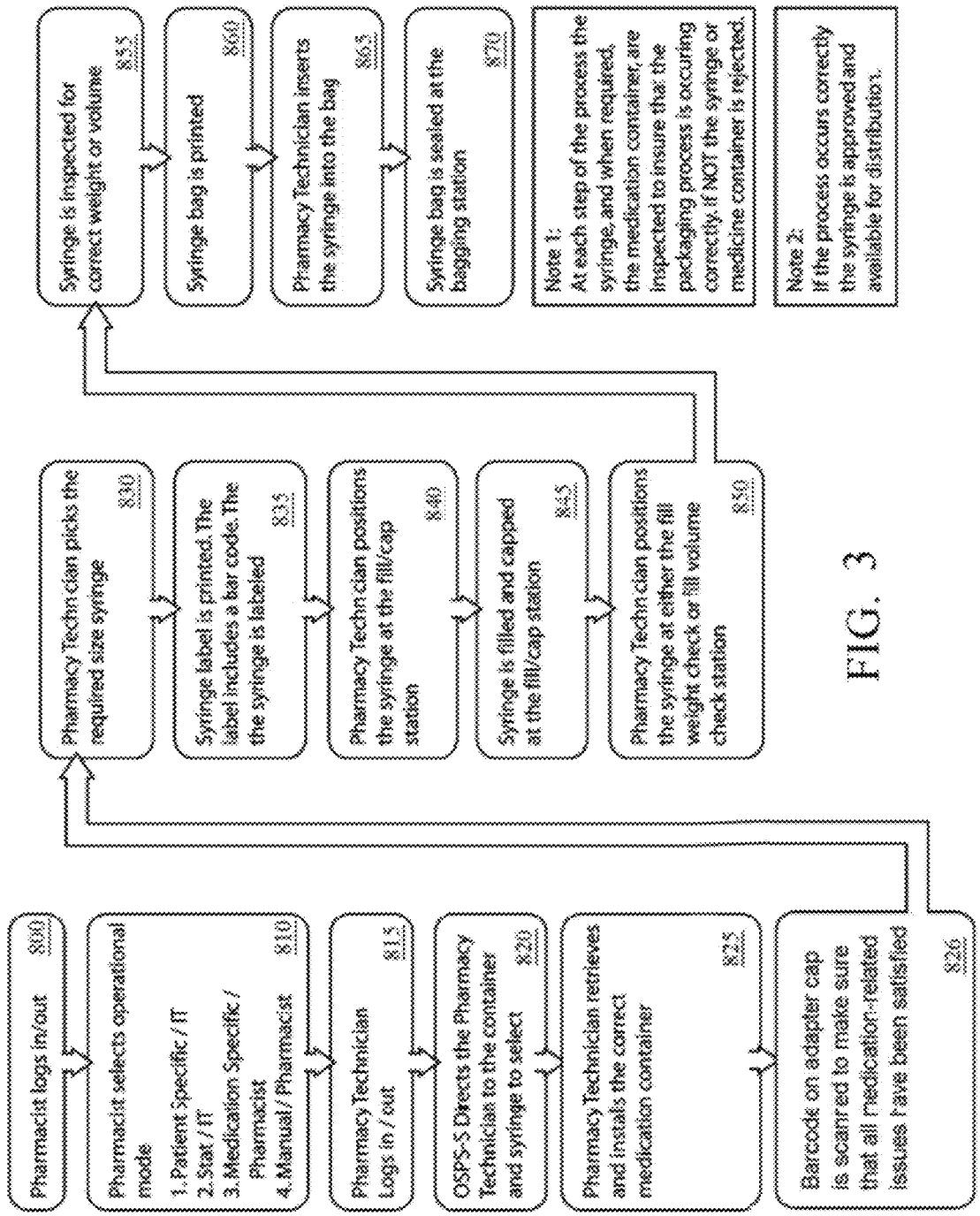
FIG. 3 is a more detailed flowchart of the substeps of the batch fulfillment process 750 of FIG. 1.

With reference both to FIGS. 2-3, at step 800 a pharmacist must log into the OSPS local computer to use the system.

At step 810, the pharmacist selects the desired OSPS operational mode. Currently four modes of operation are envisioned:

1. Patient Specific—Hospital Directed
   a. The Doctor writes the prescription and enters it into the Hospital Host Computer System.
   b. The prescription is reviewed by the Pharmacist. If it is okay, the prescription is sent to the Local OSPS Computer where it is batched. Batches will typically be run 2-3 times a day.
   c. The Local OSPS Computer first sorts all the batched prescriptions in alphabetically order by name.
   d. The prescriptions are then sorted by size of fill from smallest to largest. The total amount of each medication required for that batch run is totaled. The Local OSPS Computer checks to ensure that there is a sufficient amount of product for each medication required to complete the batch.
2. STAT (Rush Order)—Hospital Directed
   a. The Doctor writes the prescription and enters it into the Hospital Host Computer System.
   b. The prescription is reviewed by the Pharmacist.
   c. The prescription order indicates that the prescription needs to be administered soon to the patient.
   d. If the OSPS System 100 is currently being used, the Pharmacist can decide to either stop all current prescriptions being packaged or wait until completion. Either way, the Local OSPS Computer processes the singular rush order.
3. Medication Specific—Pharmacy Directed
   a. This mode allows production-scale filling of a large number of syringes with the same medicine and the same fill volume. Some medication will need to be inventoried in advance of the Doctor's prescription. This mode provides the pharmacist with the opportunity to package certain liquid oral products such as vitamins and popular standard dose medications on a more cost-effective basis than buying them already pre-packaged.
   b. The Pharmacist will manually enter in a production order for the medication into the Local OSPS Computer.
   c. The Pharmacist will specify the medication name, size of fill, the information that will go onto the syringe label, the information that will go onto the bag that the syringe is packaged in, and the amount of syringes that are to be packaged for that production run.
4. Manual—Pharmacy Directed
   a. Not all hospitals have an existing electronic prescription system installed that permits the electronic transmission of the Doctor's prescription to the hospital pharmacy. Consequently, the OSPS can be operated on a manual basis whereby the prescriptions are entered into the system under the Pharmacist's supervision.

One skilled in the art should understand that other operational modes include a Patient Priority mode in which all medications/oral prescriptions for a specific patient are processed sequentially before moving on to the next patient. The invention is herein described in the context of Patient Specific—Hospital Directed Mode which is the most typical mode of operation.

At step 815 an operator (pharmacy technician) logs in.

At step 820 the OSPS local computer directs the operator to select the appropriate medicine container from Storage Facility 2, and an appropriate syringe from storage bin 3 (FIG. 2).

At step 825, the operator retrieves the appropriate medicine container from Storage Facility 2 (under system guidance) and installs it at the syringe fill/cap station 5.

At step 826, the barcode on the adapter cap is scanned to make sure that all medication-related issues have been satisfied (refrigeration, light-sensitive storage, expiration, etc.).

At step 830, the operator retrieves the appropriate size syringe from storage bin 3.

At step 835, the operator prints a syringe label at syringe label printer and labeler station 4 indicating in both human and machine readable forms (i.e. text, barcode or RFID tag) the type, concentration, expiration, etc. of the medication it will contain. The label includes a bar code (preferably a 2D barcode though other labels such as RFID may be used. The label is adhered to the syringe barrel.

At step 840, the operator positions the empty syringes at the syringe fill/cap station 5.

At step 845, the syringe is filled and (optionally) capped at the fill/cap station 5. The OSPS system automatically fills the syringe with the medicine by insertion of the syringe nozzle into the adapter cap, and withdrawal of the plunger. The system optionally caps the syringe and presents it to the operator.

At step 850, the operator positions the filled syringe at check weight and/or volume station 6 and at step 855 the syringe is inspected for correct weight or volume. These actions are logged.

At step 860 a syringe bag is printed/barcoded at bag printing and sealing station 7, and at step 865 the system verifies the bag is printed correctly. If so, the operator is permitted to insert the filled/capped syringe into the barcoded/labeled bag.

At step 870 the syringe bag is sealed at the bag printing/sealing station 7. The packaged syringe can then be distributed to the patient.

At each step of the above-described process the OSPS system employs comprehensive track-and-trace inspection/validation of the syringe and, when required, the medication bulk container, to insure that the packaging process is occurring correctly and to compile an audit trail of the current and past locations (and other information) for each syringe.

If the process fails then as seen at step 760 of FIG. 1 the syringe or medicine container is rejected. If the process occurs correctly then as seen at step 770 of FIG. 1 the syringe is approved and available for distribution. The core method and possible variations are herein implemented in several detailed embodiments of a system suitable for preparing single oral syringe doses. Various alternate embodiments of the invention may omit selected steps (and their performance station) where such is/are not required. The needs of the operating institution and the cost aspect of automating certain steps may direct which steps/stations (if any) are to be performed manually by an operator interfacing with the apparatus and which may be automated.

Referring back to FIG. 2, each station of the pharmacy automation system 100 for oral syringes is described below in more detail.

Medication Container Login & Orientation Station 1

The first station in the process of the present invention is Medication Container Login & Orientation Station 1 at which the bulk medicine is prepared for use in the system 100. Medication Container Login & Orientation (MCLO) Station 1 is a standalone desk unit that provides a facility for inputting needed information into the OSPS database via scanner 95 and data entry terminal 96, apply barcodes as needed via label printer 97, decap bulk containers 104 (see FIG. 5) at decapping station 93, and refit them with an adapter cap (as will be described) at capping station 94. All of the scanner 95, data entry terminal 96, label printer 97, decapping station 93, and capping station 94 are commercially available components. MCLO Station 1 is standalone so that it can be positioned as desired. Medicine for oral syringes is provided in liquid form in a container with a manufacturer-applied safety cap. An object of the present invention is to be able to insert a syringe nozzle into the containers to withdraw a proper dose of medicine into the syringe. As indicated, this requires removal of the manufacturer's cap and replacement with a specialized adapter cap having a penetrable seal for insertion of an oral syringe nozzle (or alternatively, manufacturer's conforming their packaging such that they provide their products to hospitals with an adapter cap pre-applied).

Figure 5A:
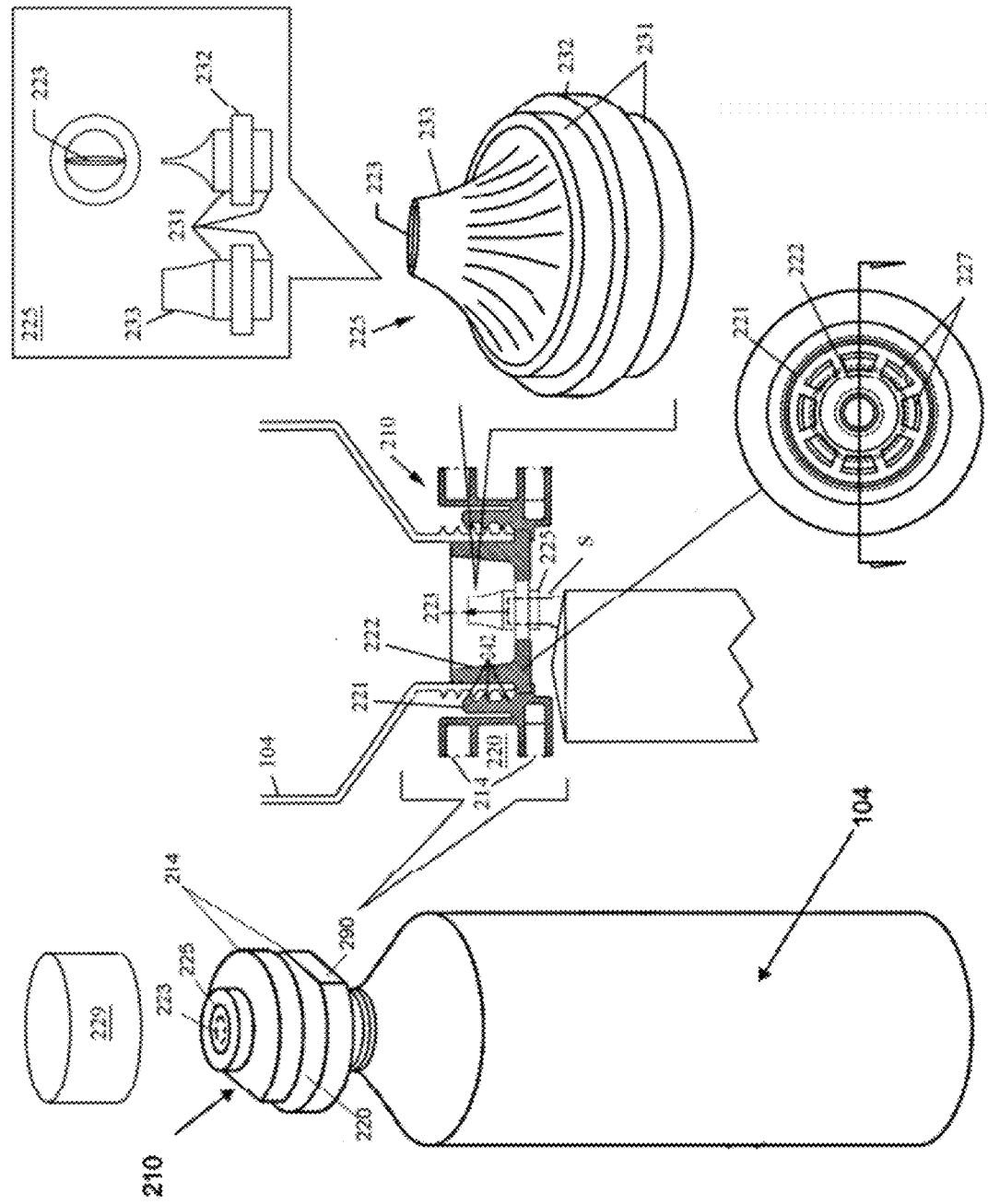
FIG. 5A is a composite view of an adapter cap 210 according to an embodiment of the present invention.
Figure 5C:
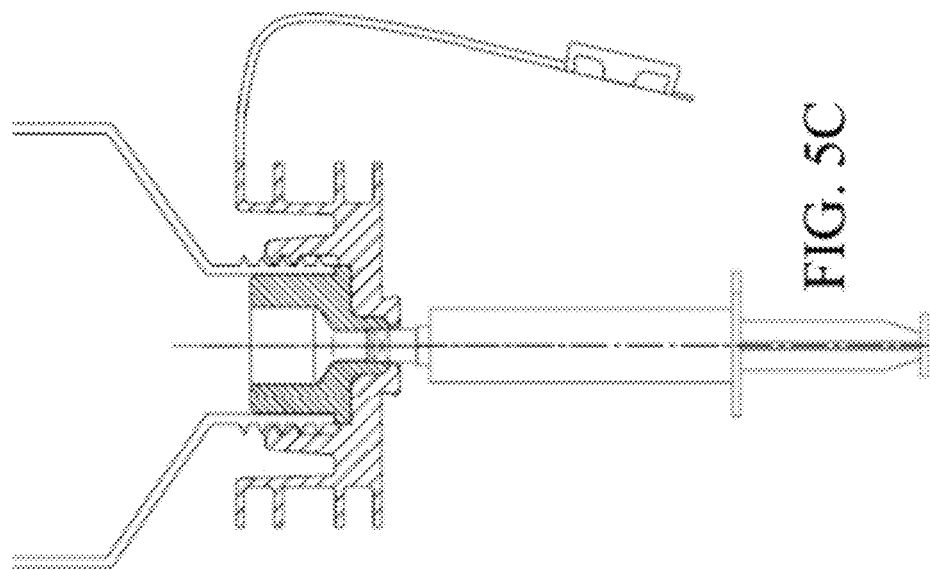
FIG. 5C is a side view of an adapter cap 210 with tether according to an embodiment of the present invention with the syringe in place.
Figure 5B:
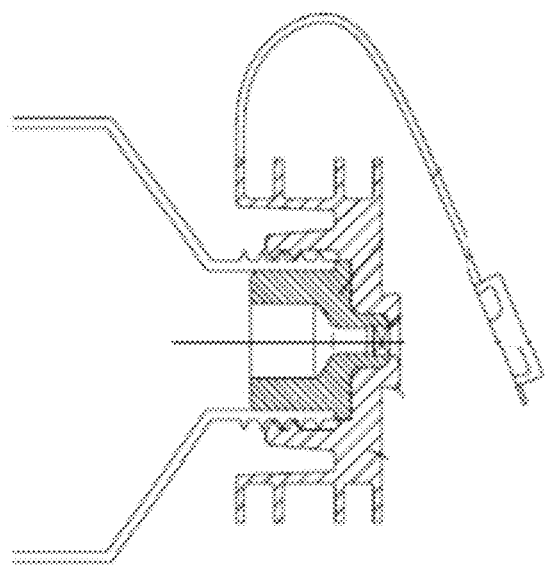
FIG. 5B is a side view of an adapter cap 210 with tether according to an embodiment of the present invention.

FIG. 5 is a composite view of an adapter cap 210 according to the present invention which is adapted to fit a variety of medicine bottle types and sizes. Despite the variability in OEM medicine bottle types and sizes, the adapter cap 210 affords a consistent external configuration and dimensions, providing an interface between any standard medication container with the present OSPS system 100. It also facilitates insertion of the oral syringe nozzle into those standard medication containers. As described in detail below, each adapter cap 210 is an annular member defining an internal barrel with an aperture 223 at one end, an elastomeric seal 225 over the aperture for penetration by the nozzle of a syringe S, and opposing flanges 214 separated by a groove 220. An overcap 229 may be provided as a protective cover to the adapter cap 210. The opposing flanges 214 encircle the cap body and define the annular groove 220 there between for positive engagement by the dispensing apparatus 100 so as to enable syringe filling operations. All adapter caps 210 are barcoded in advance with a unique identifier number. If desired, one of the flanges 214 may be defined with a peripheral flat area for displaying a bar code 290 or, alternatively, bar code 290 may be located atop the uppermost flange 214 (on the top of the cap). The other flange 214 may also be defined with a peripheral flat area for indexing the orientation of the medicine container 104. One flat area enables orientation of the adapter cap 210 in a known position. The other flat area better presents the identifying information such as a barcode for automated sensing or reading of the information. The flat areas also enable or facilitate automated or manual tightening of the threaded connection between the neck of the container 104 and the cap 210. The barcode flat and the orientation flat are preferably parallel to one another on opposite sides of the adapter cap 210 and are also longitudinally offset so as to be distinguishable. The known relationship between the orientation flat and barcode flat facilitates manual or automatic of container positioning and orientation with the dispenser and automatic sensing of the same. In addition to or in place of one or more of the flats, strategically located holes or recesses in the top surface of the cap may be provided.

One skilled in the art should also recognize that identifying information can be expressed by barcode printing or labeling directly on the cap 210 or the cap may serve as a vehicle to carry an "RFID" tag. The plastic resin used to mold the cap may be formulated to contain an ingredient that would allow direct printing on the cap with either ink or a laser without the need for or use of adhered paper or similar labels. The top of the cap may also be used to affix, print or etch the barcode either by direct printing or adhesive label.

With reference to the middle inset of FIG. 5, an exemplary embodiment of an adapter cap 210 is depicted. Adapter cap 210 comprises a generally annular cap body preferably formed of a polyethylene, polypropylene, polyvinyl chloride or a similar synthetic polymer. The cap body is formed with an annular outer wall 221 for supporting the cap 210 against the outer surface of the medicine container and supporting opposing flanges 214, and a coaxial annular inner wall 222 for supporting the cap 210 against the inner surface of the medicine container and supporting and centering the elastomeric seal 225 within the neck of the medicine container. The flanges 214 may be hollowed as shown to conserve material, solid, or may be open around their periphery. Also, the flanges 214, annular outer wall 221 and coaxial annular inner wall 222 may be integrally formed (such as by molding), or may be separate but attached as shown. The annular inner wall 222 is open at one end and constricted at the other by an inwardly projecting annular flange 229 which defines a typically circular aperture 223 through the cap body 220 for access to the contents of the medicine container 104 as will be described. The elastomeric seal 225 is mounted in the aperture 223 to create a sealed but penetrable passage for the syringe S nozzle.

The outer wall 221 of the adapter cap 210 may be defined by a simple inwardly-threaded connection for screw-insertion onto the threaded container 104 neck. However, the great variety of manufacturer thread pitches and container 104 neck sizes weighs in favor of a more universal-fit adapter cap 210. This is possible by providing the outer wall 221 of the adapter cap 210 with a series of integrally formed inwardly-directed circular gripping ribs 242 for gripping the neck of a bottle 104 by its threads. As the neck of a bottle 104 is forced into the central void, the ribs 242 engage the threads on the outside of the neck of the bottle and flex to permit the threads to pass. Once past, the ribs 242 spring back toward their original position and press against the neck to engage the threads and secure the adapter cap 210 to the container 104. The variable size of the central void due to the flexure of the resilient ribs 242 permits the adapter cap 210 to accommodate some variation in outside neck diameter and thread finish, and create a fluid-tight seal without the need for a specific thread pitch. The coaxial annular inner wall 222 abuts the interior of the container 104 neck, centers the adapter cap 210, and centrally supports the elastomeric seal 225 within the neck. If desired, the annular inner wall 222 may be separately formed as an elastomeric insert to effectuate a fluid seal between the inner wall 222 and the smooth inside surface of the neck of the bottle 104. Similar to the outer wall 221, inner wall 222 may also be formed with a plurality of outwardly-directed annular ribs or wipers to improve the seal, or may contain an outwardly-facing O-ring for the same purpose. In this case inner wall 222 may be a separate element inserted into the outer wall 221 of the cap body and secured in place by ultrasonic welding or otherwise.

To improve the resiliency of the inner wall 222 and/or outer wall 221 either/or can be segmented by notches partially interrupting the continuous walls, thereby forming several (preferably eight) "spring finger" segments attached to the body and arrayed about its axis. The bottom inset of FIG. 5 illustrates this axial array of segments 227 which, if formed in outer wall 221 effectively snap over the threads on the exterior of the neck of the medicine container 104. The serrated segments 227 are first to advance down the threaded neck and align the neck for a better seal with the adapter cap 210 body. The same can be done on the inner wall 222 to improve resiliency, again forming several (preferably eight) "spring finger" segments to abut the interior of the medicine container 104 neck.

Even with the resilient ribs 242 and segments 227 each adapter cap 210 won't fit all sizes of container 104, and so it is envisioned that several (approximately eight) sizes of adapter cap 210 will be needed.

The elastomeric seal 225 is fitted within the aperture 223 of the flange of inner wall 222. In its simplest form the elastomeric seal 225 may be a resilient, penetrable membrane with a small hole or slot (such as a pinhole) punched at its center, and preferably formed of silicone or other rubber. The hole in the seal 225 expands as the tip of a syringe S is inserted to permit pressurization of the container 104 and/or filling of the syringe (by vacuum) as described below. On withdrawal of the syringe tip the resilient elastomeric seal 225 returns to its original shape closing the hole and preventing leakage of the fluid contents of the bottle 104. However, a flat elastomeric seal 225 with a hole or slot has been found to drip slightly.

To prevent dripping, a preferred embodiment of the elastomeric seal 225 is shown in the right-most inset of FIG. 5, which improves the engagement with the nozzle of the syringe S. Seal 225 is formed with a hollow cylindrical section 231 circumscribed by a flange 232 for mounting within (or to) the coaxial annular inner wall 222 of the adapter cap 210 body. The cylindrical section 231 leads to a pronounced duck-bill protrusion 233 that tapers to a distal tip, with aperture 223 (preferably slotted) continuing out through the duck-bill protrusion 233. The duck-bill protrusion 233 serves as a flap valve against the nozzle of the syringe S and expands to receive the nozzle of the syringe S.

The duck-bill configuration is advantageous because it creates a seal around the syringe S nozzle prior to the nozzle forcing open the duck bill slit. Likewise, upon exit, the duck-bill closes prior to the syringe nozzle breaking its seal against the interior. This tends to self-relieve pressure and prevent dripping.

The adapter cap 210 is typically applied to the container 104 as shown at left and inserted into the Medication Container Login & Orientation Station 1 (FIG. 1) in an upright orientation as shown. The adapter cap 210 allows the attached medicine container 104 to be manually staged by the upper and lower flanges 214 and thereby gripped by the Medication Container Login & Orientation Station 1 in order for the container 104 to be to shaken (when needed) and inverted 180 degrees into a fill position (as in FIG. 5 middle inset) for upward insertion of the syringe S. Inversion allows the fluid contents to be collected at the adapter cap 210 under force of gravity.

Referring back to FIG. 2, at MCLO Station 1 a number of bins 12 are provided for storing various sizes of adapter caps 210 as needed to fit all standard container sizes. As described above in steps 910 through 965 (FIG. 4), OSPS system 100 guidance for the manual container 104 selection process and return process (along with the adapter cap 210 and syringe S selections) is "system-guided" as described above. Each adapter cap storage compartment 12 may be enclosed by a magnetically-actuable door so that access to each location may be electronically controlled by the local OSPS computer, or illuminated by an LED light, or equipped with a light curtain so that the local OSPS computer can monitor access to the proper location.

OSPS system 100 guidance for the manual container 104 selection process employs a software module that relies on all three of the information components stored in the OSPS system database: 1) product information from the manufacturer or other external sources describing the medicines and their containers (size, dose, handling requirements, etc.); 2) prescription-specific information from the hospital identifying the prescription details and patient to receive it; and 3) OSPS runtime information such as the amount of medicine previously taken from a given bulk container. Specifically, patient-specific information from the hospital identifying the prescription details is compared to product information from the manufacturer or other external sources to determine the appropriate medicine to retrieve. The software module ascertains from the patient-specific information the appropriate amount of medicine to retrieve. This is compared to OSPS runtime information (the amount of medicine previously taken from the bulk containers 104) to determine the specific container 104 to retrieve. The location of that container 104 is ascertained from the scan of the container 104 and pre-labeled adapter cap 210 at scanning station 95, and the ensuing storage location in Storage facility 2 which was assigned via OSPS system 100 guidance. The exact container 104 location is presented to the operator who retrieves the container from the Storage facility 2. Again the Storage facility 2 may be fitted with magnetic doors, LED lamps or light curtains either to compel the proper selection, draw the operator's attention to it, or provide an alarm in case of a wrong selection. In still other embodiments the container 104 selection may be semi-automated so that the appropriate container is ejected to the operator under control of the OSPS computer.

In operation, and as described above with regard to FIG. 4 (medication container orientation and log-in process step 920), the OEM caps on medication containers 104 are manually removed and discarded at decapper 93, the OSPS local computer instructs the operator which of the adapter caps in storage 12 (FIG. 2) to select for recapping the medication container 104 (step 926), the operator retrieves the proper adapter cap 210 and applies it at capper 94. The labeler 97 generates a 2D barcode label which includes the location of Storage facility 2 that the medication container 104 is to be stored at. The operator places the 2D bar code on the adapter cap, and the 2D barcode on the adapter cap is scanned by scanner 95. All general and container specific information derived by scanning or supplemental data entry at data entry station 96 is recorded in the local OSPS computer database, including the storage location of the bulk container 104 in Storage facility 2 and the expiration date of the medication container. The operator then manually stores the container in the Storage facility 2 assigned by the OSPS computer. If the container is to be stored in light protected storage 2(c) or refrigerated storage 2(b) the track-and-trace software ensures compliance. Later, when needed to fulfill a batch of oral syringe prescriptions an operator will select (with system guidance) a container 104 of the desired medicine from the Storage facility 2 with adapter cap 210 applied, scan it at scanning station 162, and load it into a product interface 81 (FIG. 7) at the fill/cap station 5. The medicine is verified by the scanning as to proper content, available fluid volume and other attributes before being loaded at the product interface 81.

The second station in the packaging process according to the present invention is a storage bin 3 for storage of empty syringes. The syringe storage 3 preferably incorporates a separate syringe compartment for each size of syringe that the system anticipates needing in the course of a production run. Again, this manual selection process (along with other manual selections) is "system-guided" as defined above in respect to syringe S selection as well. As with medicine container 104 selection, the software module ascertains from the patient-specific information the appropriate dose of medicine to determine the specific syringe S size to retrieve. The location of that syringe S is ascertained from the database, and the exact syringe S location in syringe storage 3 is presented to the operator who retrieves it from the syringe storage 3. Again the syringe storage 3 may be fitted with magnetic doors, LED lamps or light curtains either to compel the proper selection, draw the operator's attention to it, or provide an alarm in case of a wrong selection. In still other embodiments the syringe storage 3 selection may be semi-automated so that the appropriate syringe S is ejected to the operator under control of the local OSPS computer. The selection software module calculates the most appropriate syringe S size based on the required prescription information dosage, the known volume of the syringe selections (the following standardized oral syringe sizes: 0.5 ml, 1 ml, 3 ml, 5 ml, 10 ml, 20 ml, 35 ml, 60 ml), identifies the syringe size to accommodate the fill volume of the prescription, and presents the syringe storage 3 location to the operator who retrieves the syringe from the proper magazine (with help of LED indicator, magnetic door, light curtain, ejection mechanism or otherwise).

The third station is a flag label printer/applicator 4. After retrieving the syringe S the operator inspects it for defects and, finding none, inserts the syringe into syringe label printer 4, which is a commercially available flag label printer/applicator. As described above relative to FIG. 3 (step 835), the operator prints a syringe label at syringe label printer 4. The labeler is in communication with the local OSPS computer and automatically prints self-adhesive labels bearing information regarding the prescription such as the eventual contents of the syringe (medicine type, concentration, dosage, expiration, scheduled administration, etc.) and its intended recipient (name, room number, etc.) along with a bar code identifying a central record of this information in the OSPS database. The label includes a 2D barcode though other labels such as RFID may be used. The label is adhered to the syringe barrel using known application methods. In one such embodiment the label is supported by hinged arms of the applicator and held by vacuum pressure while the applicator advances to envelope the syringe barrel with the hinged arms coming together to join the label as a flag to the barrel of syringe S. A portion of the label around the barrel must be transparent to permit dosage markings of the syringe to be clearly visible. The operator positions the empty syringe S (step 840) at the syringe fill/cap station 5.

The fifth station is the syringe fill/cap station 5 for filling the syringes S, and with optional capping capability. A scanner is resident at the syringe fill/cap station 5 to automatically scan the machine readable labels on the surface of the container 104, cap 210 and loaded syringe S to again verify that the selected items are correct. The operator loads the container 104 into the fill station at a manual product interface 81 and manually loads the oral syringe S into a loading carriage 70 (FIG. 7) of the syringe fill/cap station 5. The product interface 81 engages the container 104 and inverts it into a fixed upside down position and orientation (see FIG. 5 middle inset) for filling of the syringe. The system automatically fills the syringe S with the medicine by insertion of the syringe nozzle into the adapter cap 210, and calibrated withdrawal of the plunger. The system optionally caps the syringe and returns it to the operator.

The sixth station is an inspection station 6 which comprises a check-weigh scale. The operator uses it to weigh and/or inspect the filled syringe S to verify the syringe is as labeled, and the System 100 accepts or rejects the weighed/inspected syringe. The OSPS software calculates the target weight based on the fill size in cc's and multiplies by the specific gravity to derive weight. The specific gravity of each medication is stored in the OSPS database along with the percentage+/−% deviation that is acceptable for the actual fill weight. If the actual fill weight is in the target range, it is accepted. If not, it is rejected.

More preferably, inspection station 6 is a vision inspection station (alone or in combination with check weigh scale) to ascertain fill volume.

Figure 6:
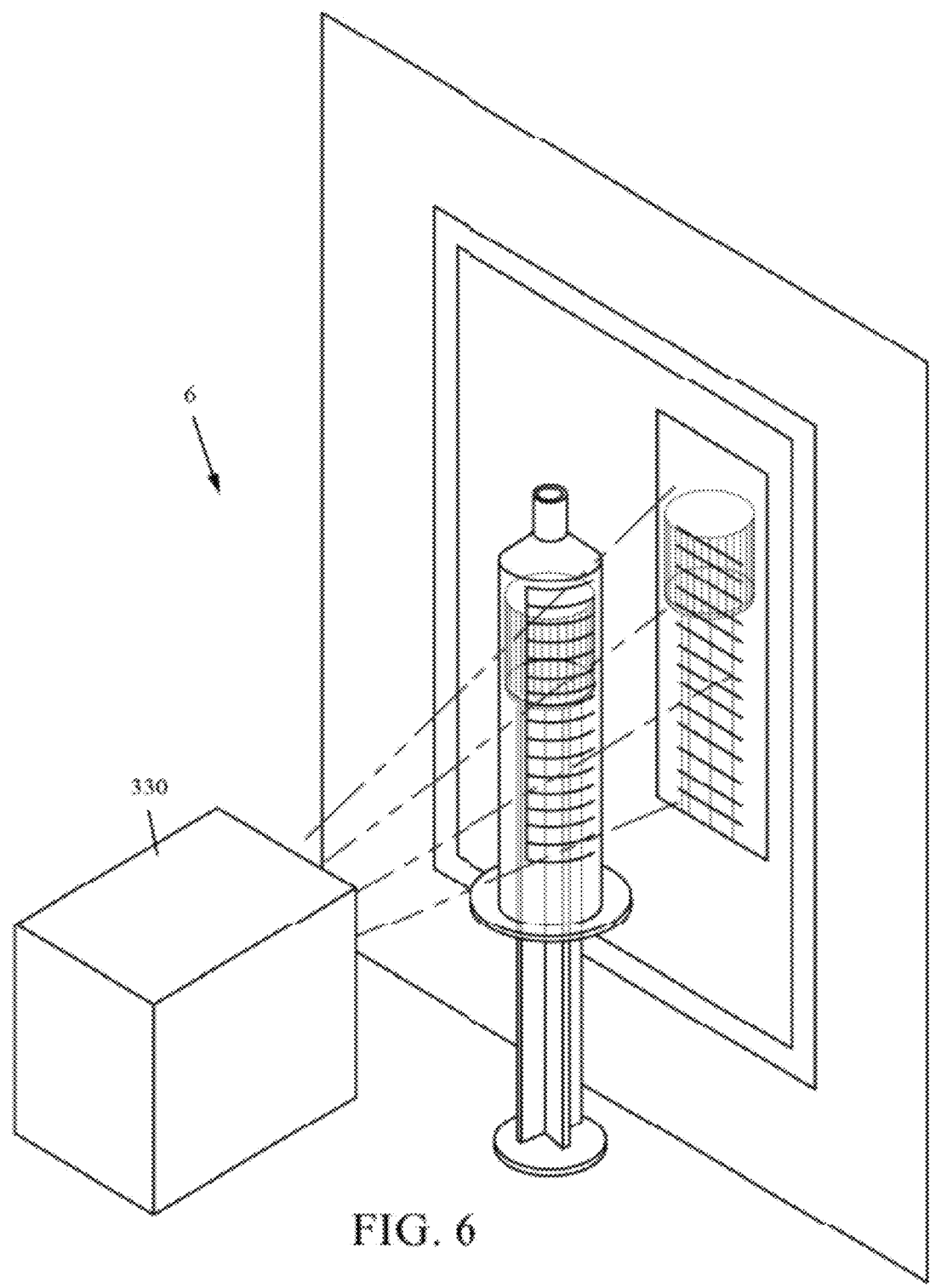
FIG. 6 is a perspective view of an exemplary vision inspection station 6.

FIG. 6 is a perspective view of an exemplary vision inspection station 6 in which syringe fill volume is inspected by a CCD imager 330 that optically detects by image analysis if the syringe S plunger is at the correct location, the volume above the plunger and below the syringe tip is filled with product, and also checks for bubbles in the product. If the syringe volume inspection device 6 determines that the syringe is filled to the correct volume with an acceptable amount of bubbles, it will be accepted. Otherwise it will be rejected.

The seventh station is a bag printing and sealing station 7. The bagging station 7 is a commercially available Hand Load Printer/Bagger for hand load labeling and bagging applications. It is networked to the local OSPS computer to automatically print the bag that the syringe S will be packaged in. The bag is printed with information regarding the prescription such as the eventual contents of the syringe (medicine type, concentration, dosage, expiration, scheduled administration, etc.) and its intended recipient (name, room number, etc.) along with a bar code identifying the same content. After printing a bag the system inspects the print on the bag to make sure that it is correct. If so, the operator is permitted to place the filled/capped syringe S in the bag, the system confirms that the syringe was placed in the bag, and the bag is then sealed.

If all the steps are completed correctly the syringes are distributed for administration to the patient.

One skilled in the art will recognize that certain steps may be completed in various alternate sequences to achieve the same result, and features may be modified or eliminated as a matter of design choice.

With combined reference to FIGS. 1-6 and additional reference to other drawings a detailed description of an embodiment of the present invention is herein provided.

At initial MCLO Station 1 an operator prepares bulk medicine containers for use at the automated syringe fill/cap station 5. Preparation entails applying an adapter cap 210 onto the neck of the bottle or container to enable the system to engage and manipulate the container 104 during the dispensing process as will be described. Again, each adapter cap 210 is pre-labeled with a unique identifying number, for example, in barcode format. Preparation of the container 104 also includes scanning, verification and recordation of adapter cap 210 information, scanning, verification and recordation of container 104 label information including content information (name, manufacturer, full volume, concentration, etc.), batch or production information and expiration information, and association of the unique adapter cap 210 number with its assigned container 104 in a medication track and trace database. Various other parameters for each medicine can be associated with each record in the database such as the maximum flow rate at which a certain medicine can be withdrawn from its storage container (i.e. to prevent cavitation/inaccurate fills), the storage temperature (ambient or refrigerated), the required frequency of shaking/agitation of each medicine to keep any particulate matter properly suspended/distributed (e.g. between each syringe fill dispense cycle or only at the start of a series of syringe fill dispense cycles). As an example, each barcode (or possibly RFID tag or other label) preferably references the following information:

Batch number
Expiry date
Storage instructions
Product name
Strength
Name of the active ingredient(s)
Dose form
Warning statements
FDA number
Product need to be shaken before use? If so, how often?
Product need to be refrigerated before use? If so, temp?
Volume of original bulk medication container?

The information available from the pharmaceutical manufacturer's barcode on the medication container varies from manufacturer to manufacturer. The operator is prompted to enter any missing data directly into the computer data entry terminal 96 at MCLO Station 1. The information from the pharmaceutical manufacturer's barcode label plus the variable information is stored in the medication container database which is linked to the medication container by the adapter cap barcode label. The adapter cap 210 identifying number is linked to the container 104 to which it is attached in the medication track and trace database. It is also important that each container 104 is marked in both human and machine readable forms (i.e. text, barcode or RFID tag) as to the type and concentration of the medication it contains along with various other information, to enable visual inspection.

The containers/bottles 104 are typically manufacturer-supplied although custom containers/bottles may be used for purposes of the present system. If the storage containers or bottles 104 are provided by the manufacturer, 20 mm, 24 mm, and 28 mm neck diameters are typical. The bulk containers may be provided in a specified, standardized format by the manufacturer, or the medicines may be refilled into standardized containers onsite.

If a custom storage container 104 is used the neck diameter is a uniform, known size. In either case, the storage containers 104 may be retained in an upright or inverted position and are preferably equipped with adapter cap 210 that allows dispensing while preventing air infiltration that leads to premature spoilage of the contents. Proper adapter caps 210 are either substituted for the manufacturer's onsite or supplement the manufacturer's cap.

With regard to FIG. 2, the container gripping apparatus 81 effectively flips the container 104 from the position shown about a 180 degree arc to an inverted fill position out front. Once inverted in the fill position, an oral syringe S is advanced into the elastomeric seal 225 of the adapter cap 220 and is sealed therein (see FIG. 5). The oral syringe may be entirely evacuated such that its plunger is advanced all the way into its barrel or the oral syringe may have a calibrated amount of a gas (such as air or nitrogen) in front of the plunger in the barrel. The syringe plunger may be withdrawn to draw the fluid into the barrel. Where a gas is present in the syringe, the plunger may be first advanced so as to force the gas into the container 104. The plunger is then withdrawn to draw the fluid into the syringe. Introduction of the gas into the container 104 slightly pressurizes the container initially and prevents the development of negative pressure within the container which would inhibit fluid flow. When the syringe is filled to the proper volume it is withdrawn.

Referring back to FIG. 2, the operator returns the prepared medicine container 104 with its adapter cap 210 in the medicine Storage Facility 2 where it remains until called for. The system software monitors the contents of the medicine Storage facility 2 in terms of both identity of the prepared medicines available to be dispensed and the quantity of each medicine. The content of the Storage facility 2 is continually updated as the medicine is dispensed and the system is able to predict based on current pending prescription and historical dispensing information when the current available container of any given medication will be empty so as to advise the operator to prepare a replacement quantity of such medicine prior to emptying the existing container. Medicines exceeding their expiry dates are also identified by the system to be discarded by the operator.

After retrieving the syringe from syringe store 3 of empty syringes S to be filled as described above, the operator inspects it for defects and, finding none, inserts the syringe into a syringe label printer/applicator 4. The labeler 4 is in communication with the central controller and prints self adhesive labels bearing information regarding the prescription such as the eventual contents of the syringe (medicine, dosage, scheduled administration, etc.) and its intended recipient (name, room number, etc.) along with a bar code identifying a central record of this information. The label is printed, scanned (inspected) and, if approved, applied to the syringe using known application methods. In one such method the label is supported by the hinged arms of the applicator by vacuum pressure while the applicator advances to envelop the syringe barrel with the hinged arms coming together to join the label as a flag to the barrel. A portion of the label around the barrel must be transparent to permit dosage markings of the syringe to be clearly visible.

Figure 7:
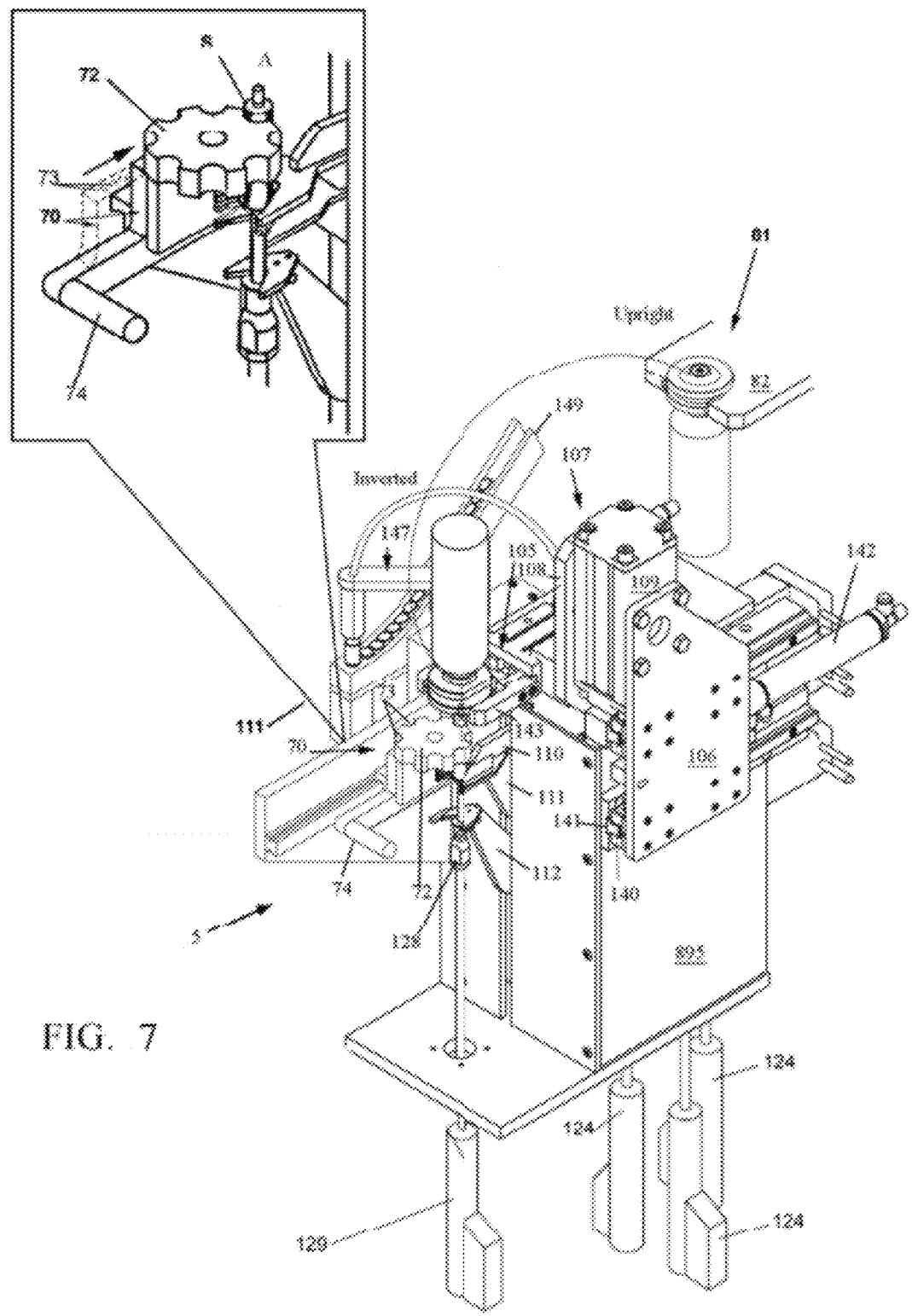
FIG. 7 is an enlarged perspective view of a semi-automated syringe fill station 5 for filling the syringes S, shown with optional capping capability.

FIG. 7 is an enlarged perspective view of a semi-automated syringe fill station 5 for filling the syringes S, and with optional capping capability. The syringe S is manually loaded by the operator into the loading carriage 70 of the syringe fill/cap station 5, preferably with the plunger partially withdrawn from the barrel. The loading carriage 70 is a manually-moveable element having starwheel indexer 72 with a series of semicircular wells 73 of differing sizes positioned to receive syringes of various sizes and a push-handle 74 for pushing each loaded syringe into a loading position. After loading the syringe, the operator must position the starwheel indexer 72 so that the appropriately-sized well engages the syringe. The operator selects the well 73 corresponding to the particular syringe to be filled. The advancing syringe in carriage 70 cooperates with the starwheel indexer 72. The cooperation of the advancing syringe in carriage 70 with rotary starwheel indexer 72 prevents the indeed of a wrong-sized syringe, and indexes both the position of the syringe (moving it 90 degrees counterclockwise into the fill position), and the orientation of the syringe (for syringes with offset nozzles it indexes the nozzle to the same angular position when the syringe is in the fill position). The enlarged inset of FIG. 7 shows an expanded cross-section of the internal mechanics of the starwheel indexer 72. With syringe loaded into a well of carriage 70, the operator pushes the push-handle 74 which spins the syringe 90 degrees counterclockwise around to the loading position (A). In the present embodiment both carriage 70 and rotary starwheel indexer 72 are provided with semi-circular wells conforming to the following standardized oral syringe sizes: 0.5 ml, 1 ml, 3 ml, 5 ml, 10 ml, 20 ml, 35 ml, 60 ml. The need to manually index the proper well of carriage 70 to that of starwheel indexer 72 prevents the in-feed of a wrong-sized syringe. The starwheel indexer 72 then indexes both the position of the syringe (moving it 90 degrees counterclockwise into the fill position), and the orientation of the syringe (for syringes with offset nozzles it indexes the nozzle to the same angular position when the syringe is in the fill position).

Figure 8:
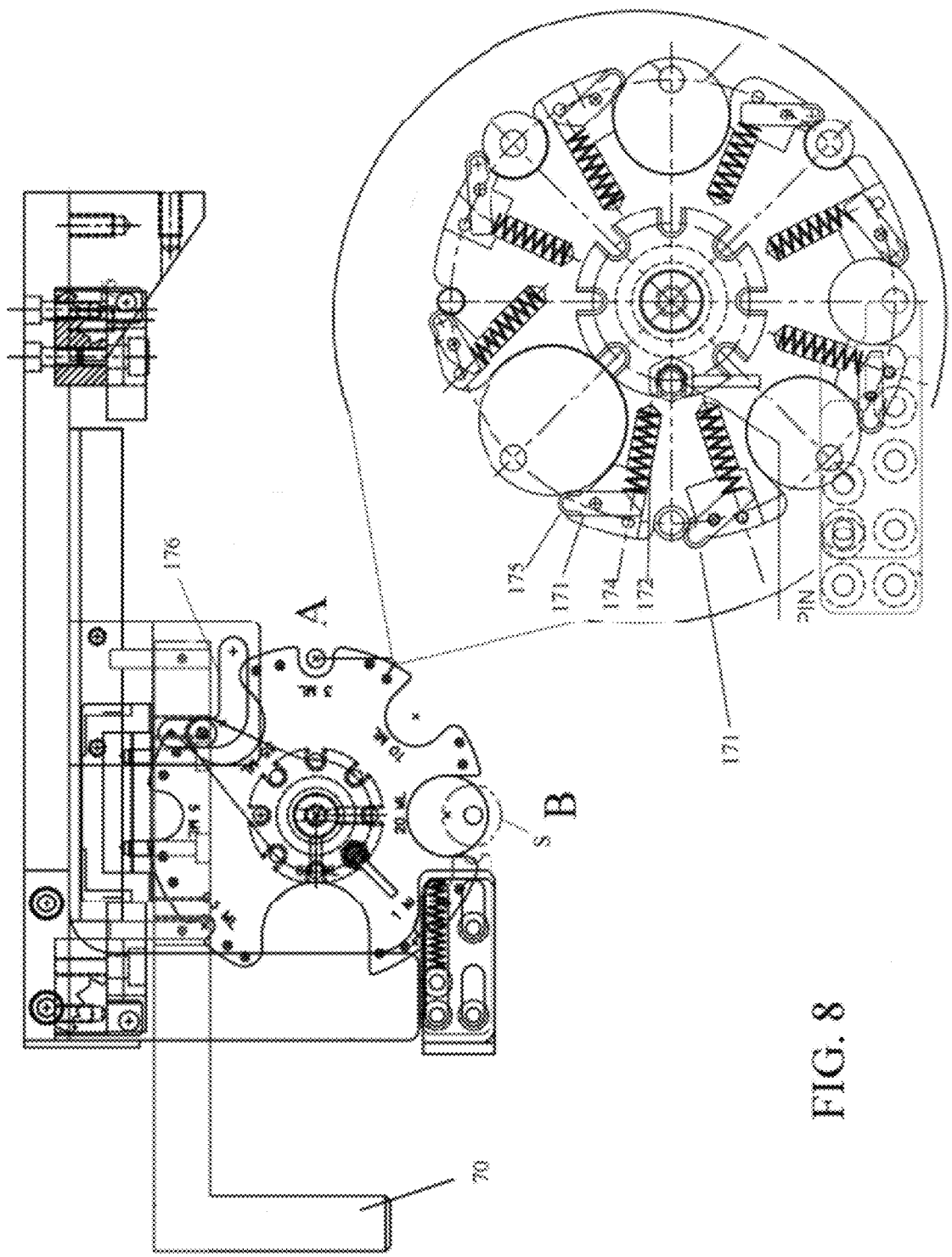
FIG. 8 is a top cross-section of an exemplary syringe in-feed mechanism.

As seen in FIG. 8, the syringe S is held captive in the starwheel indexer 72 by a series of internal spring-fingers 171. Each spring finger 171 is a short strut pivotally mounted in an alcove 174 between adjacent wells of starwheel indexer 72, with a roller wheel 175 (or bearing surface) at its distal end impinging into the well, and biased inward by a compression spring 172. The slight impingement of the roller wheel 175 into the well traps the syringe S therein, and the spring bias of spring 172 keeps it trapped unless forcibly removed.

Approximately half way to the loading position a nozzle positioning mechanism 176 grabs the syringe nozzle and (if the nozzle is offset from center-axis) rotates it to a fixed position so that all syringes arrive at the loading position (A) with their nozzles uniformly oriented. Once in the loading position (A) the syringe is filled as described below. When finished, the operator pulls out the carriage 70 and this indexes syringe S around to an unloading position (B). The operator optionally caps the syringe, and removes the filled/capped syringe.

Referring back to FIG. 7, once in the fill position the syringe is engaged by a series of arms, upper 110, middle 111 and lower 112, that grip and operate the syringe S in order to effectuate the filling process.

Figure 9:
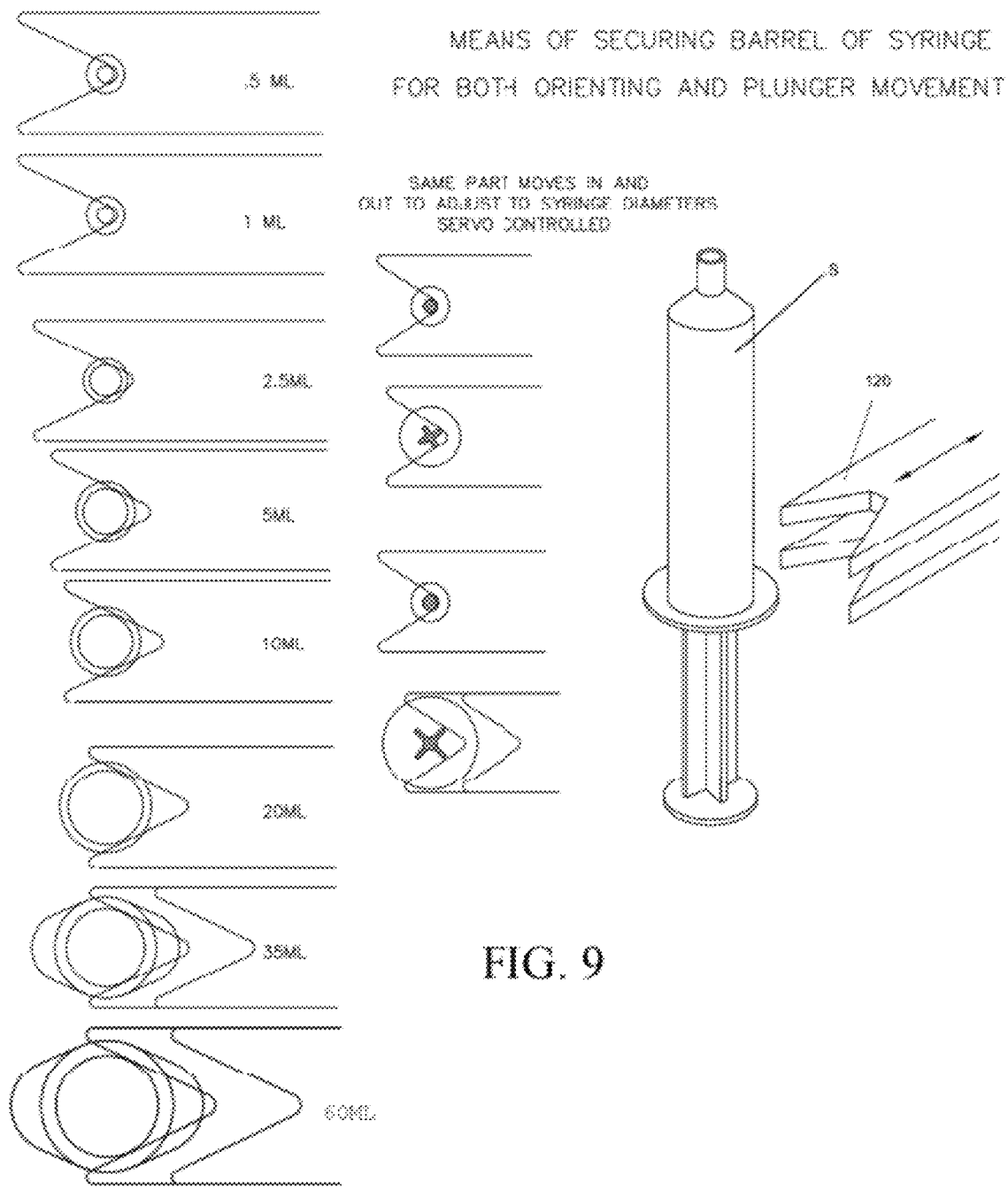
FIG. 9 is a composite view of the syringe gripping arms 110, 111 and 112 terminating in a pair of fork shaped fingers 120 that form a horizontally oriented "V" shaped opening.
Figure 10:
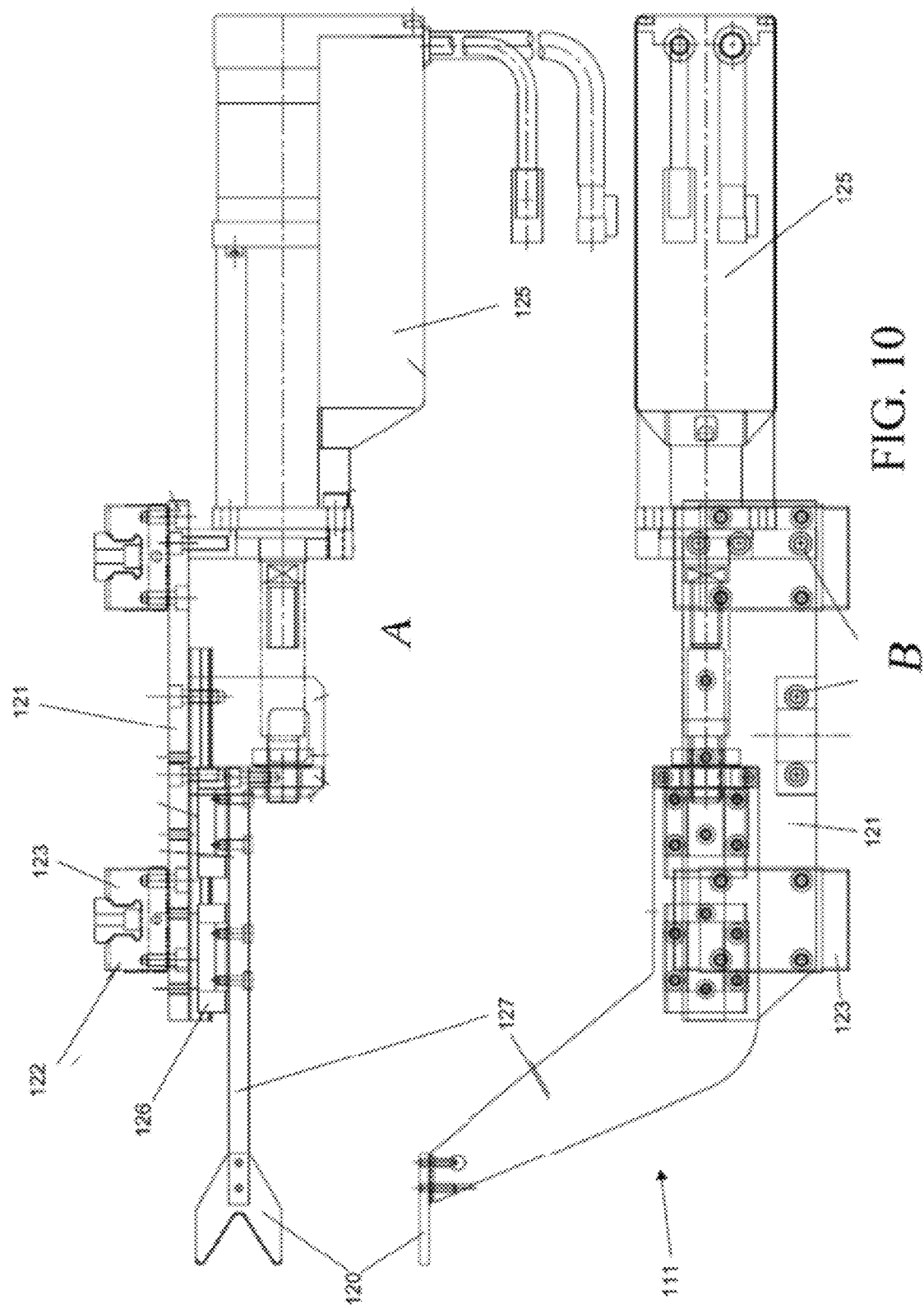
FIG. 10 illustrates an embodiment of the syringe gripping arms 111 and its drive mechanism.

As seen in FIG. 9, each arm terminates in a pair of fork shaped fingers 120 that form a horizontally oriented "V" shaped opening to engage the syringe barrel and plunger cross sections regardless of the size of these elements. Each arm is independently servo controlled and slideable in both an up-down direction and a horizontal forward-back direction to facilitate engagement with and operation of the syringe and plunger. The upper and middle arms 110, 111 grip above below the syringe barrel flange, while the lower arm 112 grips the plunger flange. The local OSPS computer calculates the distance to move the lower arm 112 and plunger flange to extract the appropriate dose of medicine based on the prescribed dose volume V and known radius or diameter of the syringe S size retrieved. The linear travel distance H equals V/□r' where the radius r is stored in the database. The linear travel distance H constitutes the distance that the lower arm 112 needs to travel to pull the correct amount of medicine into the syringe S. The local OSPS computer then controls the movement of fill arms 110, 111, 112 in accordance with the calculated distance H, and may also account for other variables such as medicine viscosity, volume of fill, etc. to optimize either the linear travel distance H or the filling force exerted or filling time taken along that distance. With reference to FIG. 10, a preferred embodiment of the present invention provides the upper, middle and lower arms 110, 111 and 112, respectively, in a single stacked configuration each having a horizontally fixed base member 121 riding on a pair of ball slides 122 on a set of guide rails 123 vertically oriented with the housing 895 (of FIG. 7). Vertical movement of each base member 121 on the guide rails 123 is controlled by a linear servo 124 situated below and extending into the housing 895. Each arm 110, 111, 112 is also provided with a horizontal reaching element 127 slideably mounted horizontally to each base member 121 so as to ride up or down the guide rails 123 with the base member 121 while being extendable or retractable in the horizontal to engage the syringe S. Horizontal extension and retraction of the reaching members 127 is controlled by a horizontally oriented linear servo 125 fixedly mounted to each base member 121 and engaged to the proximate reaching element 127, each which is itself mounted via a horizontally oriented ball slide assembly 126 affixed to the base member 121. The forked fingers 120 are horizontally disposed at the distal ends of the reaching elements 127. In this way the horizontal and vertical motion of each arm 110, 111, 112 is individually controllable in two dimensions.

Referring back to FIG. 7, in addition to the upper, middle and lower arms 110, 111, 112, a plunger lifting arm 128 extends upward from below to depress the plunger of the syringe S into the barrel as will be described. The plunger lifting arm 128 is controlled by a linear servo and is vertically oriented. In certain embodiments the lower arm 112 may serve both the plunger pull-down (withdraw) and plunger lift (depress) operations.

Prior to inserting the syringe into the syringe fill/cap station 5, the operator will have selected from the Storage facility 2 the appropriate, prepared container 104 from which to dispense the proper medicine into the syringe S. After verifying its contents by reading the human readable label, the container is manually loaded into the syringe fill/cap station 5 at the manual product interface 81, as shown in FIG. 7. The interface comprises an offset yoke 82 that engages the adapter cap 210 between the upper and lower flanges 214, suspending the container 104. The operator signals "ready" by pressing a button at the control interface.

Prior to filling, the scanner at the syringe fill/cap station 5 reads the machine readable label on the surface of the container 104 or cap 210 to again verify that the selected container contains the correct medicine.

Once verified to be the correct, a fill arm 105 comprising a pair of grippers 143 are moved over the yoke 82 around the flanges capturing the container 104 in position. The grippers 143 are slideable toward and away from each other and are provided with a series of grooves and ridges in their opposing faces to cooperatively engage with those of the container adapter cap 210 to facilitate secure engagement with and gripping of the cap.

Movement of fill arm 105/gripper arms 143 over the yoke 82 may be accomplished by slideably mounting the fill arm 105 on an arm carriage 106, and mounting the arm carriage 106 on a horizontal ball slide 140 and track 141 or tracks on or in the housing of the syringe fill/cap station 5 so as to be advance able forward and backward between a syringe S in the loading carriage 70 at one end of the fill station and the product interface 81 at the other end. A linear actuator 142, preferably pneumatic, is provided to slide the arm carriage 106 on its track(s) 141 between the forward and back positions or to its home position between the two extremes. The arm carriage 106 is generally a vertically oriented plate member supporting a fixedly attached, pneumatically driven container rotator/inverter assembly 107. The container rotator assembly 107 controls rotation of a rotator arm 108 about a horizontal axis. Fixedly attached at a distal end of the rotator arm 108 is the fill arm 105 including grippers 143 disposed to engage the adapter cap 210 of the container 104 when the container is situated in the product interface 81. The container rotator/inverter assembly 107 may include a conventional servo motor 109 with perpendicular axis attached at the lower end of the rotator arm 108. This way, after capturing the container 104, the servo 109 flips the container 180 degrees forward, inverting it, and moving it into a fill position and orientation for filling of the syringe S. If the medicine in container 104 must be shaken, the servo 109 first shakes the container back and forth before flipping it.

During fill operations the upper, middle and lower arms 110, 111 and 112 are initially in a horizontally retracted state. When the syringe S is loaded, the upper and middle arms 110, 111 are extended so that the syringe is received within the V-notch and the fingers 120 are engaged to the surface of the barrel (upper arm) and plunger (middle arm) (see FIG. 7) such that the barrel flange is between the upper and middle arms. The upper and middle arms 110, 111 then slide vertically toward each other to tightly grip the barrel flange between them. The opposing surfaces of the upper and middle arms 110, 111 may be provided with a resilient and/or high friction surface to securely engage the barrel flange. The lower arm 112 engages the plunger above the plunger flange in a similar manner while the lift arm 128 extends upward to engage the distal end of the plunger. The lower and lift arms 112, 128 are brought together to engage trap the plunger flange between them.

Simultaneously, the arm carriage 106 is drawn back under control of its actuator 142 such that the gripper assembly 109 engages the adapter cap of the medicine container in the product interface 81 securely gripping the cap and engaging the container 104 between fingers 143. The arm carriage is then advanced forward to withdraw the container 104 from the product interface 81. If needed, the rotator arm 108 is actuated in a back-and-forth motion to agitate or shake-up the medicine within the container 104. Once mixed (if necessary) the rotator arm 108 is rotated fully forward to invert the container over the syringe S such the adapter cap is aligned over the tip of the syringe. The syringe is then lifted by coordinated movement of the arms 110, 111, 112, 128 such that the nozzle is sealingly engaged within the elastomeric insert 225 of the adapter cap 210.

If the syringe S is entirely evacuated at this stage (i.e. the plunger is fully depressed within the barrel), the lower arm 112 is initially dropped, withdrawing the plunger from the barrel and drawing the medicine into the syringe. As noted, in certain embodiments the syringe may have a predetermined amount of air in the barrel to pre-pressurize the container 104. In such a situation the position of the plunger (and hence the volume of air in the barrel to be injected into the container) is determined by the system based on known parameters of the medicine, the container volume and its current fill level, and the plunger is positioned accordingly prior to insertion into the adapter cap by relative movement of the upper, middle, lower and lifting arms 110, 111, 112 and 128. Upon insertion of the tip in the adapter cap the plunger is first fully depressed by the lift arm 128 to pressurize the container and subsequently withdrawn by the lower arm 112 at a predetermined rate to fill the syringe S with desired amount of medicine without cavitation.

When the syringe is filled to the desired level, the arms 110, 111, 112 and 128 are lowered in unison and the syringe S is withdrawn from the adapter cap 210 and the elastomeric insert 225 returns to it closed/sealed position. If desired, the syringe plunger may be further withdrawn from the barrel slightly by relative movement of the lower arm 112 as the nozzle I withdrawn to draw in any medicine left in the elastomeric insert 225 so as to avoid drippage.

With the syringe withdrawn, the rotator arm 108 (FIG. 7) rotates to lift the container 104 into an upright position and the lower and lift arms 112, 128 disengage the plunger. The upper and middle arms 110, 111 return the syringe to the loading carriage 70, where the handle 74 can be withdrawn for retrieval by the operator.

The (optional) automated capper 147 may place a cap on the open tip of the filled syringe, fed from an inclined capping chute 149. Where capping is not automatic, the operator may manually place a cap over the tip prior to weighing.

Figure 11:
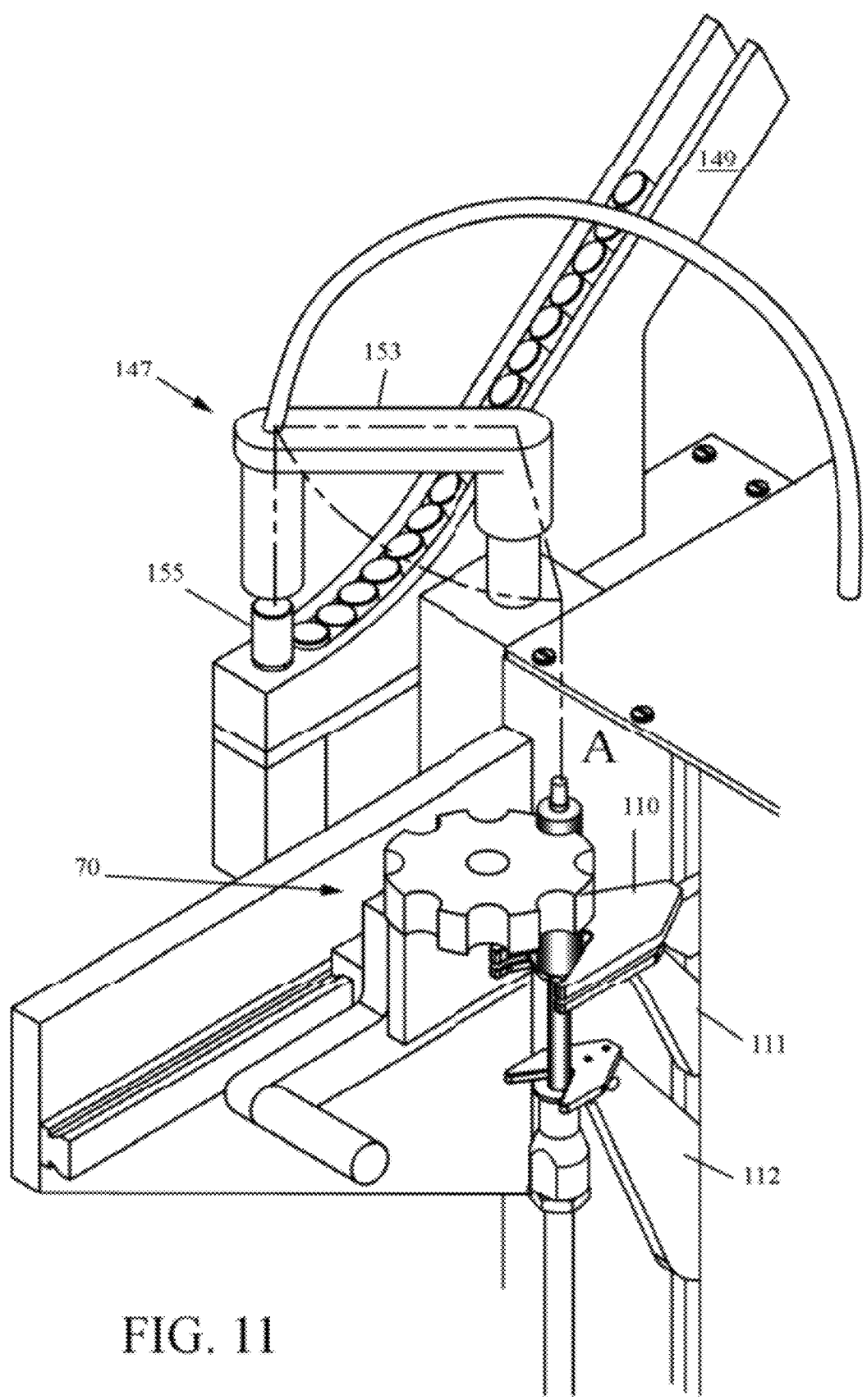
FIG. 11 is an enlarged perspective view of an automated capper 147 and inclined capping chute 149.

FIG. 11 is an enlarged perspective view of the automated capper 147 and inclined capping chute 149. Automated capper 147 is a robotic capper under control of the Local OSPS computer with a servo-controlled positioning arm 153 and pneumatic capping mechanism with a distal cap-gripping chuck 153. The positioning arm 153 is positioned over caps fed from chute 149 and picks and places them on the inverted syringes while held in arms 110-112 in the loading position (A) in carriage 70.

During batch operation a series of syringes S to be filled with the same medicine may be queued and loaded in sequence by the operator for filling. When no more syringes are to be filled with the particular medicine, the local container 104 is returned to the product interface 81 to be removed and returned under local OSPS Computer guidance to the medicine Storage facility 2 by the operator, who may retrieve another medicine and replace it in the product interface 81 for the next medicine to be dispensed.

Referring back to FIG. 2, after retrieval from the loading carriage 70 the operator places the syringe on inspection system 6 to cross check the weight and/or volume of the filled syringe against the expected weight/volume. The tare weight check is based on the known weight of the empty syringe and the volume of the prescribed medicine. The vision inspection entails an optical inspection based on the location of the syringe S plunger, the volume above the plunger and below the syringe tip, and bubble check. If the inspection station 6 determines that the syringe is filled to the correct volume and/or weight with an acceptable amount of bubbles, it will be accepted. Otherwise it will be rejected.

The labeled, filled and capped syringe is then bagged at bagger 7 for distribution to the patient, the bag itself being labeled in a similar manner as to the syringe. Bagger 7 may be any suitable commercially-available bagger with a network-capable bag printer, bag storage/dispenser, and heat seal assembly. A variety of automatic "tabletop bagger/printers" are available for this purpose.

Figure 12:
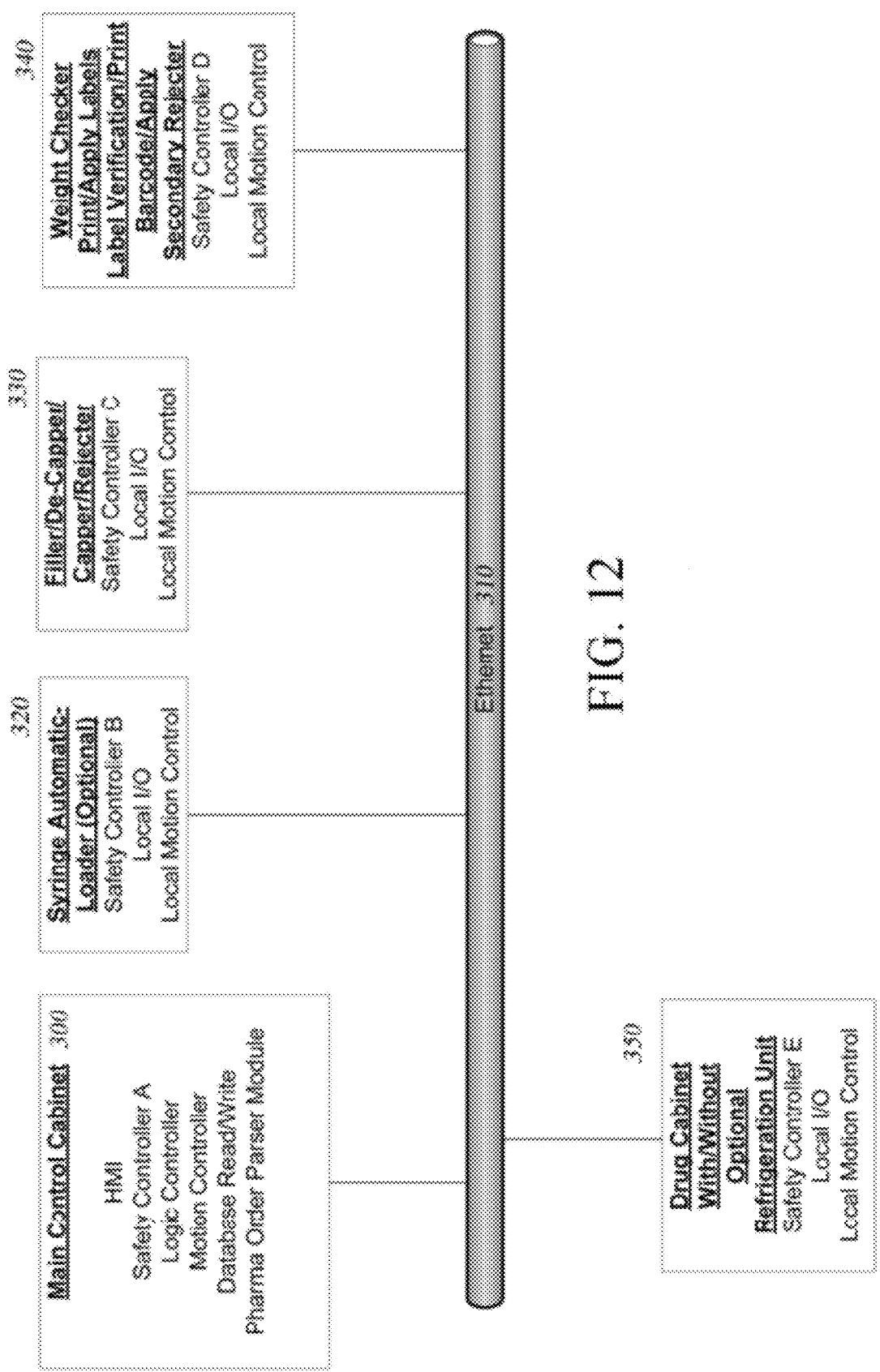
FIGS. 12 and 13 illustrate an exemplary control system architecture for the system 100 of FIGS. 2-11.
Figure 13:
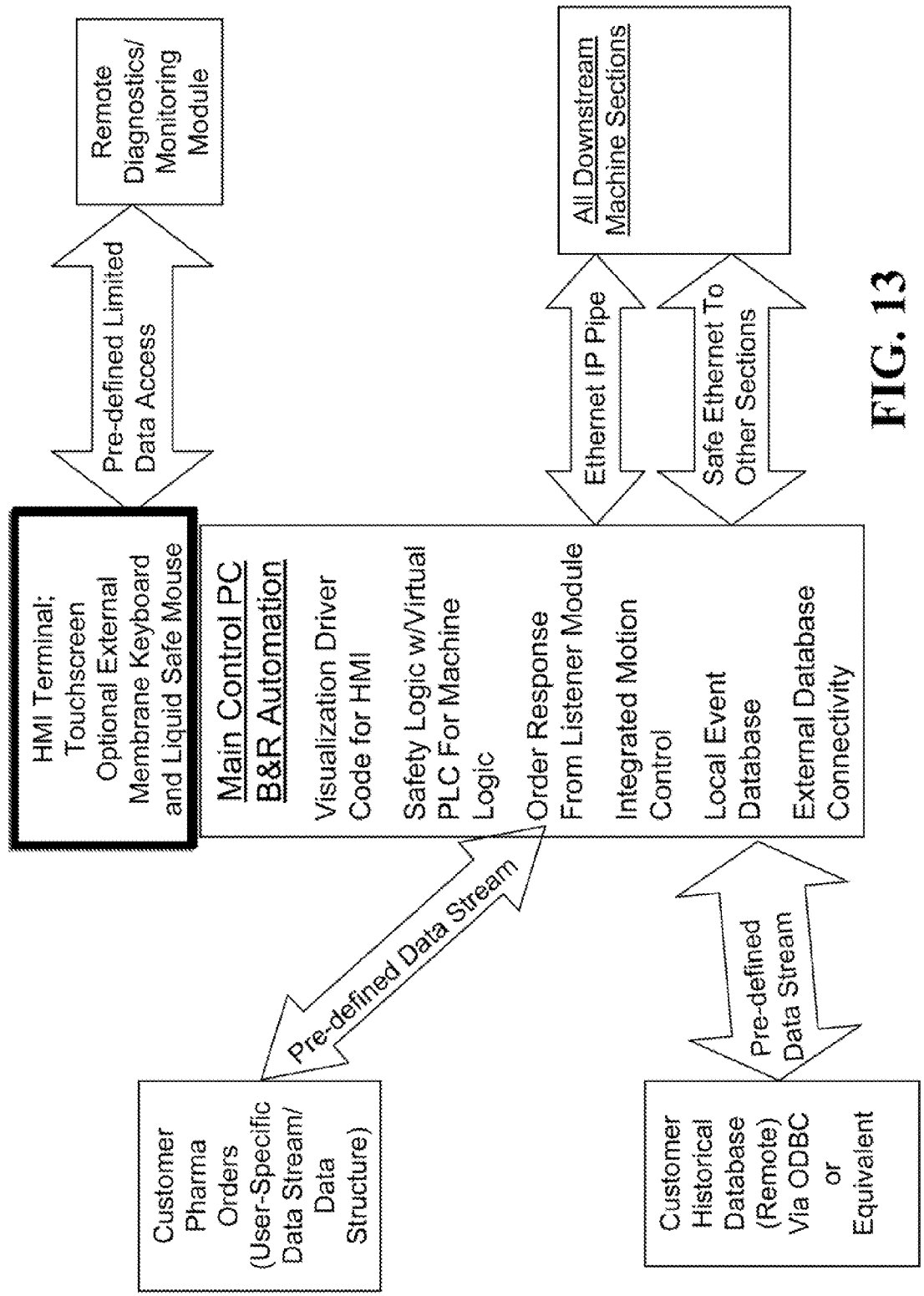

With reference to FIGS. 12 and 13, a control system architecture for the system 100 is disclosed in which a main controller 300 is provided in communication with a series of sub-controllers for one or more station steps via a communications backbone 310, in the depicted case, via Ethernet. The main controller 300 is preferably a microprocessor based microcontroller or PC containing a processor core, memory, and programmable input/output peripherals. The controller contains a system safety controller, logic controller, top level motion controller and human-machine interface for interaction with a system operator. The main controller 300 further incorporates a database read/write module for interaction with a local or remote customer (patient) records database and local event database for managing downstream component operation. An order listener/parser module is provided for receiving orders from an external pharmacy/prescription entry and management system maintained by the institution. The parser can be custom formatted to discern and populate order information based on a user specified data stream and structure.

Sub-controllers are provided for all downstream machine sections such as a Syringe Auto-loader 320 (if robotic arms are used as per below), Filler/De-capper/Capper/Rejecter 330, Checker/Verifier and Secondary Rejecter 340 and Medicine Library 350. The sub-controllers are each provided with a safety controller, local input/output system and local motion controller integrated with the main controller 300 via the communications backbone 310. The main controller orchestrates the integration and operation of the downstream machine elements as described above and controls the overall operational mode of the system 100.

The local OSPS Computer may incorporate fill weight/volume adjustment software. Specifically, the inspection station 6 is networked to the Local OSPS Computer and may provide weight or volume feedback to automatically adjust the amount of liquid transferred into the oral syringe at servo-operated syringe fill/cap station 5. The software determines if a syringe has too much or too little medicine in it. Any out-of-spec syringe will be rejected and another one will be prepared utilizing feedback from the fill weight/volume adjustment software.

Figure 15:
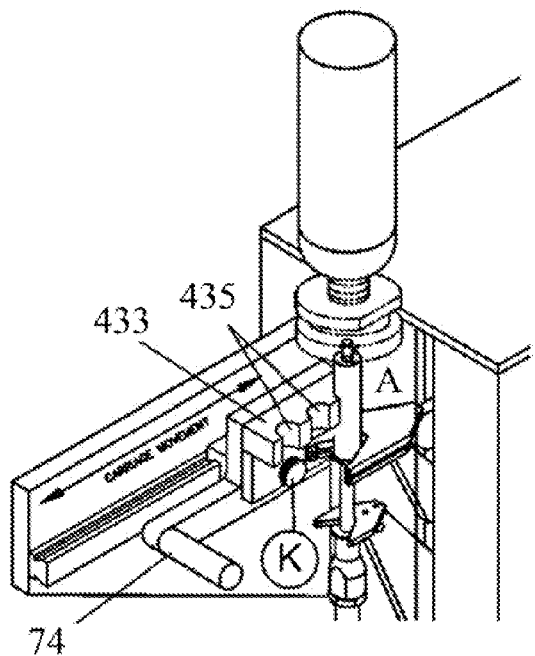
FIGS. 15, 16 and 17 show a perspective, top cross-section and end cross-section, respectively, of an alternate embodiment of the syringe in-feed mechanism.
Figure 16:
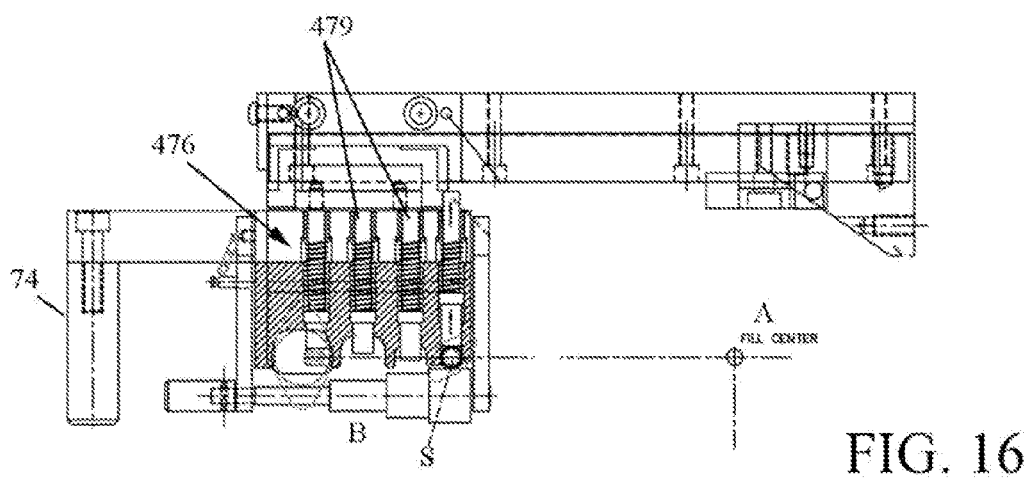
Figure 17:
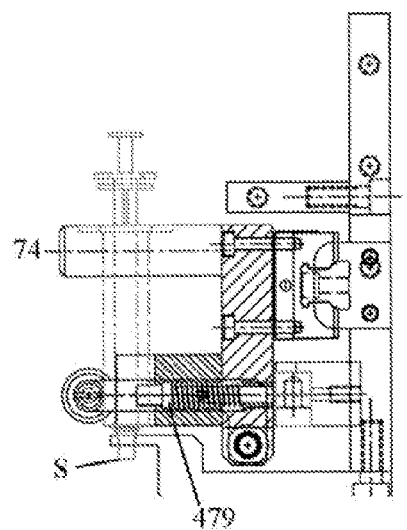

FIGS. 15, 16 and 17 show a perspective, top cross-section and end cross-section, respectively, of an alternate embodiment of the syringe staging mechanism that eliminates the starwheel indexer 72. Instead the push-handle 74 pushes a pocket block 433 linearly back-and-forth to/from the loading position (A). The pocket block 433 is a solid block formed with a plurality of yokes or pockets 435, each pocket 435 sized to seat one of the following standardized oral syringe sizes: 0.5 ml, 1 ml, 3 ml, 5 ml, 10 ml, 20 ml, 35 ml, 60 ml. The operator places a retrieved syringe S into its conforming pocket 435 and this likewise prevents the infeed of a wrong-sized syringe. The pocket block 433 then translates with handle 74 to index the position of the syringe (moving it linearly into the fill position A). A syringe tip locator 437 protrudes beneath each pocket 435 to ensure that syringes with eccentric nozzles are oriented with the off-center nozzle on generally on target. As seen in FIG. 16, a nozzle positioning mechanism 476 is embedded inside the pocket block 433 to exactly index the orientation of the eccentric nozzles. Nozzle positioning mechanism 476 comprises a plurality of spring-loaded pins 479. When a particular syringe S is placed in its proper pocket 435 a pin 479 is extended out of the pocket block 433 to act as a stop to ensure that pin 479 brings the syringe tip to the center of the fill zone A. If desired, a variety of interchangeable pocket blocks 433 may be provided, each with a subset of pocket 435 sizes, to collectively seat a wider array of syringe sizes. As with the starwheel indexer 72, pocket block 433 with spring-loaded pins 479 shuttles the syringe S and (if the nozzle is offset from center-axis) rotates it to a fixed position so that all syringes arrive at the loading position (A) with their nozzles uniformly oriented. Once in the loading position (A) the syringe is filled as described above. When finished, the operator pulls out the carriage 70 and this indexes syringe S around to an unloading position (B) as seen in FIG. 16. The operator optionally caps the syringe, and removes the filled/capped syringe.

As yet another syringe infeed assembly alternative to the starwheel indexer 72 of FIG. 8 or the pocket block 433 of FIGS. 15-17, FIG. 19(A-C) shows a perspective, top cross-section and end cross-section, respectively, of a syringe infeed pick and place mechanism that employs a carriage mounted grip arm apparatus 30 with a vertically oriented strut 31 having upper and lower gripper arms 33 extending laterally to engage the syringe S such that the unit has a profile in the form of an "F". The gripper arms 33 are stationary, but an opposing finger 32 articulates toward the gripper arm 33 to grip the syringe S barrel. Each upper and lower gripper arm 33 is provided at its distal end with a cradle to engage the outside surface of the syringe barrel. The upper and lower cradles are vertically aligned with one another and may be semicircular in form but are more preferably a "V"-shaped notch so as to engage at two points the outside surface of a tubular syringe barrel of the variety of sizes dispensed by the magazines of the syringe store. The inner surface of the "V"-notch may be provided with a high friction surface such as a rubber or other elastomeric surface to better grip the syringe. Alternately, the inner surface of the "V" notch may be provided with horizontally oriented high friction rollers to permit axial rotation of the syringe S within the cradle while preventing the syringe from slipping down/out of the cradle as described below. The cradles are oriented so as to be open in the forward direction of travel of the carriage. A pivot point is provided for each finger 32 along its length prior to the "V" notch for rotatably mounting on a bushing or bearing. The finger 32 is generally rigid along its length but may have a high friction coating or surface as with the cradle to better grip the syringe barrel. A lever arm 34 angularly offset from the longitudinal axis of the finger 32 is affixed to the finger, preferably at the pivot point. A servo motor or high speed linear actuator is connected between the lever arm 34 and the vertical strut 31 such that operation of the linear actuator causes the finger to extend over the open face of the cradle and trap/hold a syringe positioned in the cradle between the high friction surfaces of the cradle and the finger 32. The linear actuator may be electric, pneumatic, hydraulic or mechanically driven. In a preferred embodiment a separate actuator and finger assembly 32 are provided for the upper and lower arms 33. In certain alternate embodiments a single actuator may drive both an upper and lower finger 32. In certain other embodiments a single finger 32 may be provided with upper and lower cradles, although in such an embodiment the syringe barrel must span the distance between the upper and lower cradles to engage them both simultaneously. In certain other embodiments the distance between the upper and lower arms 32 may be variable. The grip arm apparatus 30 of this embodiment is slideably mounted to a carriage 40 under control of an actuator such that the grip arm apparatus 30 may be advanced perpendicular to the direction of the travel of the carriage. After capturing a desired syringe the grip arm apparatus 30 is withdrawn to a home position such that the central longitudinal axis of the syringe barrel is positioned along a centerline. The above-described automated system in all its embodiments is capable of filling and packaging oral syringes in the hospital pharmacy primarily on a patient specific, just-in-time, medication error-free, and cost effective basis. The OSPS System 100 is specifically designed to dispense from a library of up to 250-300 liquid medication into 0.5 ml, 1 ml, 3 ml, 5 ml, 10 ml, 20 ml, 35 ml, and 60 ml size syringes (both clear and amber) based on the doctor's prescription on a semi-automated basis. Its semi-automated throughput is approximately 3-5 syringes per minute based on 1-10 ml size syringes, with inspection checks at each step in the process to ensure that the syringe was packaged correctly. The Track, Trace and Validation Software documents the entire packaging process and generates an audit trail available for recall in the future. It is important to understand that the preferred embodiment of the OSPS System 100 is designed for semi-Automatic operation in which a Pharmacy Technician will select and carry the syringes S and containers 104 to each packaging station, and will return the containers 104 back the Storage Facility 2 after all of the syringes have been filled with that medication. This (rather than a fully automated system) affords all of the customary visual checks and inspections normally conducted manually, but speeds the manual process significantly and imposes a much more rigorous automated inspection/logging protocol atop the manual process to avoid all the typical human errors.

The system can be further automated by the use of robotic arms networked to the local OSPS Computer for conveying syringes S and medicine containers 104 from station-to-station in place of the operator. If this is desired then due to the extensive range required (approximately six feet) to traverse the distance of the current System 100, and the size of one robot, the inventors envision the use of two robots. A first robotic arm would be responsible for syringe selection, flag labeling and filling, while the second robotic arm would be responsible for inspection and bagging.

Figure 14:
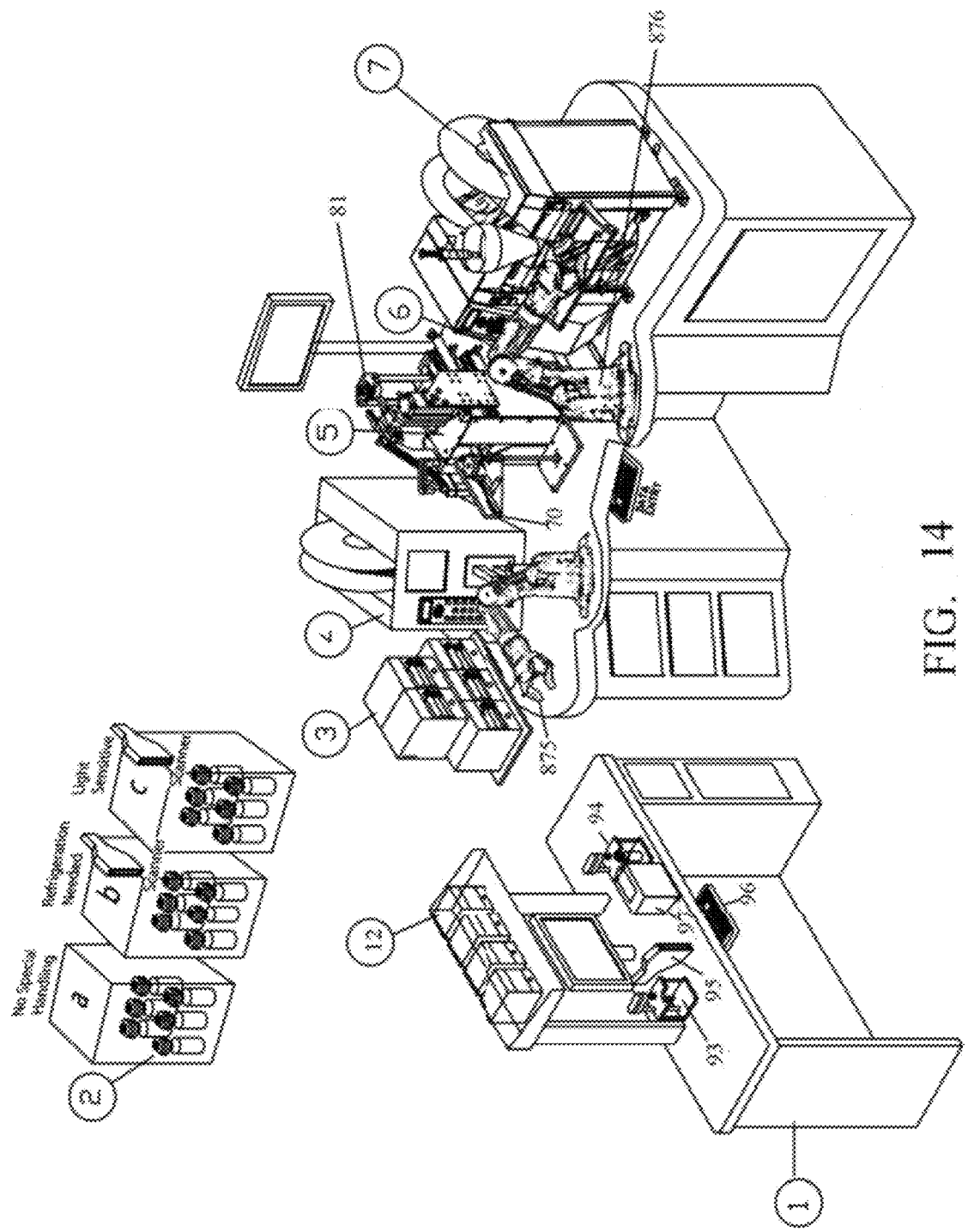
FIG. 14 illustrates another embodiment of the system 100 which includes a first robot arm 875 and a second robot arm 876 as indicated.

FIG. 14 illustrates another embodiment of the system 100 which includes a first robot arm 875 and a second robot arm 876 as indicated. The first robot arm 875 places the prepared medicine container 104 with its adapter cap 210 mounted and bar-coded into the filling staging area. The first robot arm 875 then moves to select the proper syringe from syringe storage 3, and next holds the syringe S in place for flag labeling at labeler 4. Once labeled the barcode is identified through the robot arm 875 ability to hold the label in front of the scanner for detection and identification as to the parameters for filling, including medication type, fill volume, servo plunger movement speed, refrigeration etc. Possibly, robot arm 875 could retrieve a container from Storage facility 2, and if refrigerated hold the refrigerated container next to a temperature sensor to ensure it was properly refrigerated. Arm 875 would then move container 104 into the fill/cap station 5.

Once filled and capped the second robot arm 876 would take the syringe and place the filled, capped and labeled syringe into the check-weigh/vision sensing inspection station 6 for inspection of fill volume. Once completed and accepted as correct, second robot arm 876 would place the syringe into the bagging system 7 and return to accept another filled, capped, labeled syringe.

The foregoing fulfills prescription orders in a just-in-time environment, and solves the problems inherent in the handling of all the myriad prescription containers containing the pharmaceuticals to be dispensed, as well as variously-sized oral syringes, bringing them together in a controlled environment to quickly and accurately fill and label each syringe and to verify its work as it proceeds in order to avoid medication errors in the process.

Figure 20:
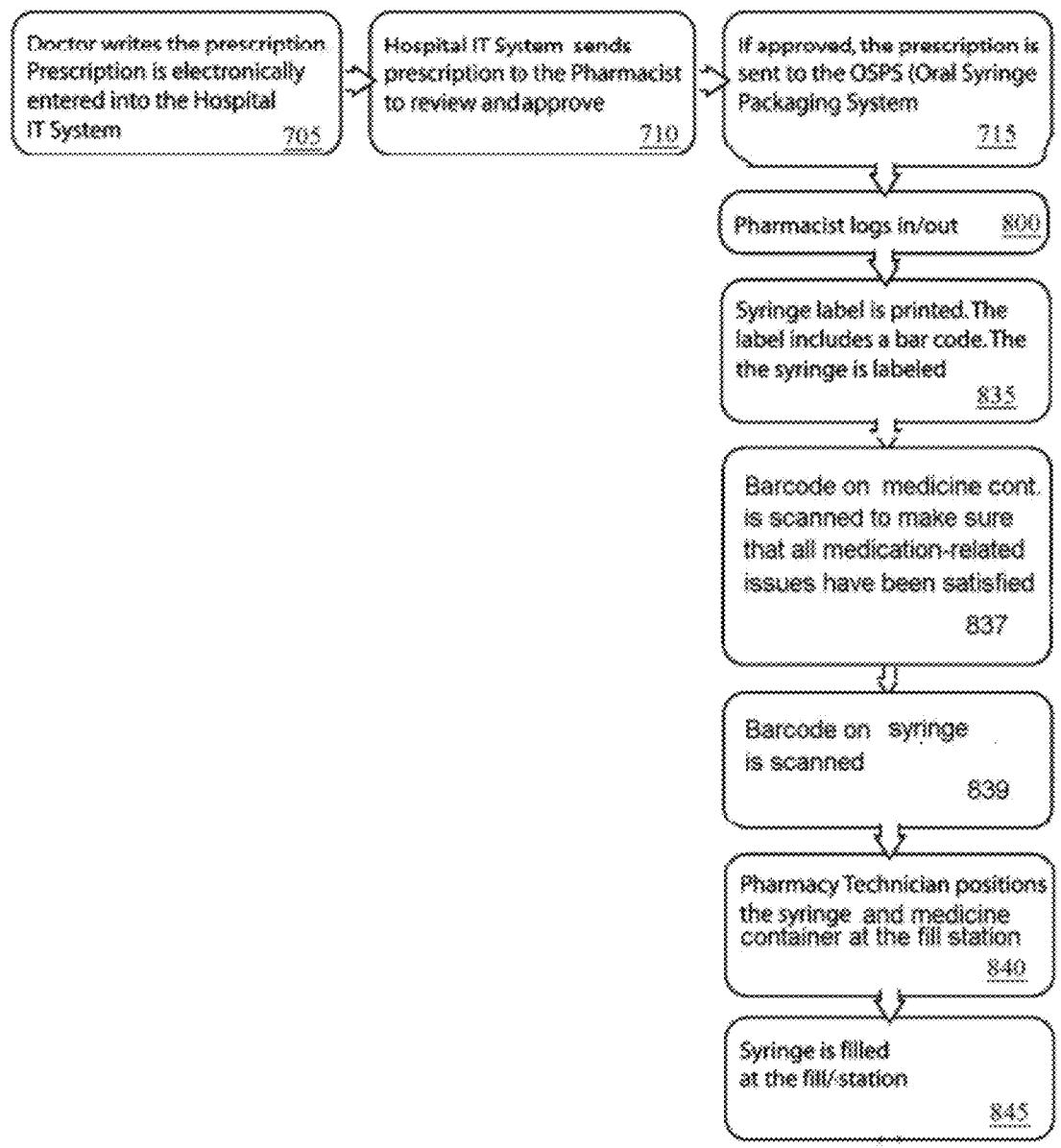
FIG. 20 is a flow diagram illustrating the method of use of the simplified embodiment.

In other cases, where a lesser degree of automation is required at significantly lowered costs, a simplified syringe filling and labeling system is offered. This system does not require the specialized adapter cap previously described. Rather, this system uses a Baxa AdaptaCap™ already in use by many hospital pharmacies. The system does not require that a special barcode label with information on the medication be generated and attached to the cap or medicine container. Instead, the manufacturer's barcode on the container is utilized. Refer to FIG. 20 for a flow diagram of the syringe filling and labeling process. A track, trace and control system is similar to the OSPS previously described is provided. The objective of the simplified syringe filling and labeling system is to ensure that the proper medication is filled into the syringe and that the syringe is labeled correctly. If an optional weight check or volume check station is utilized, the proper amount of fill can be verified.

FIGS. 18A-C are a perspective stepwise composite view of a simplified filling system with manually-adjustable medicine container grippers. The simplified embodiment is envisioned to be a bench top filling station. Rather than indexed medicine container and syringe in-feeds and servo-operated gripper fingers, the operator manually selects the appropriate medicine container 104 and syringe S size. In FIG. 18A, the medicine container 104 is manually positioned between at least one and preferably two pair of opposed self-centering gripper fingers 920, which converge to grip the container by the body and preferably also by the neck for stability. The spacing between the opposed gripper fingers 920 is manually adjustable by control knobs 930 for each pair, each control knob 930 operating by worm gear or other suitable mechanism to close the respective pair of gripper fingers 920 about the container 104, thereby centering and anchoring it, or conversely to open them for release. An adjustable stop 952 provides positive positioning of the adapter cap 904. Similarly, the syringe S is manually positioned between at least one and preferably two pair of opposed self-centering gripper fingers 910, which converge to grip the syringe S by the body. The spacing between the opposed gripper fingers 910 is manually adjustable by control knobs 940 for each pair, each control knob 940 likewise operating by worm gear or other suitable mechanism to close the respective pair of gripper fingers 910 about the syringe S, thereby centering and anchoring it, or conversely to open them for release. Since this embodiment does not grip the adapter cap 904, the adapter cap used in this embodiment need not be as comprehensive as cap 225 shown in FIG. 5. Rather any manufacturer-supplied adapter cap may be used provided that it forms a leak-proof seal with the syringe S nozzle. Thus, any conventional cap, such as Baxa's AdaptaCap™ bottle adapter cap may be used (as shown in U.S. Pat. No. 4,493,348).

Figure 18:
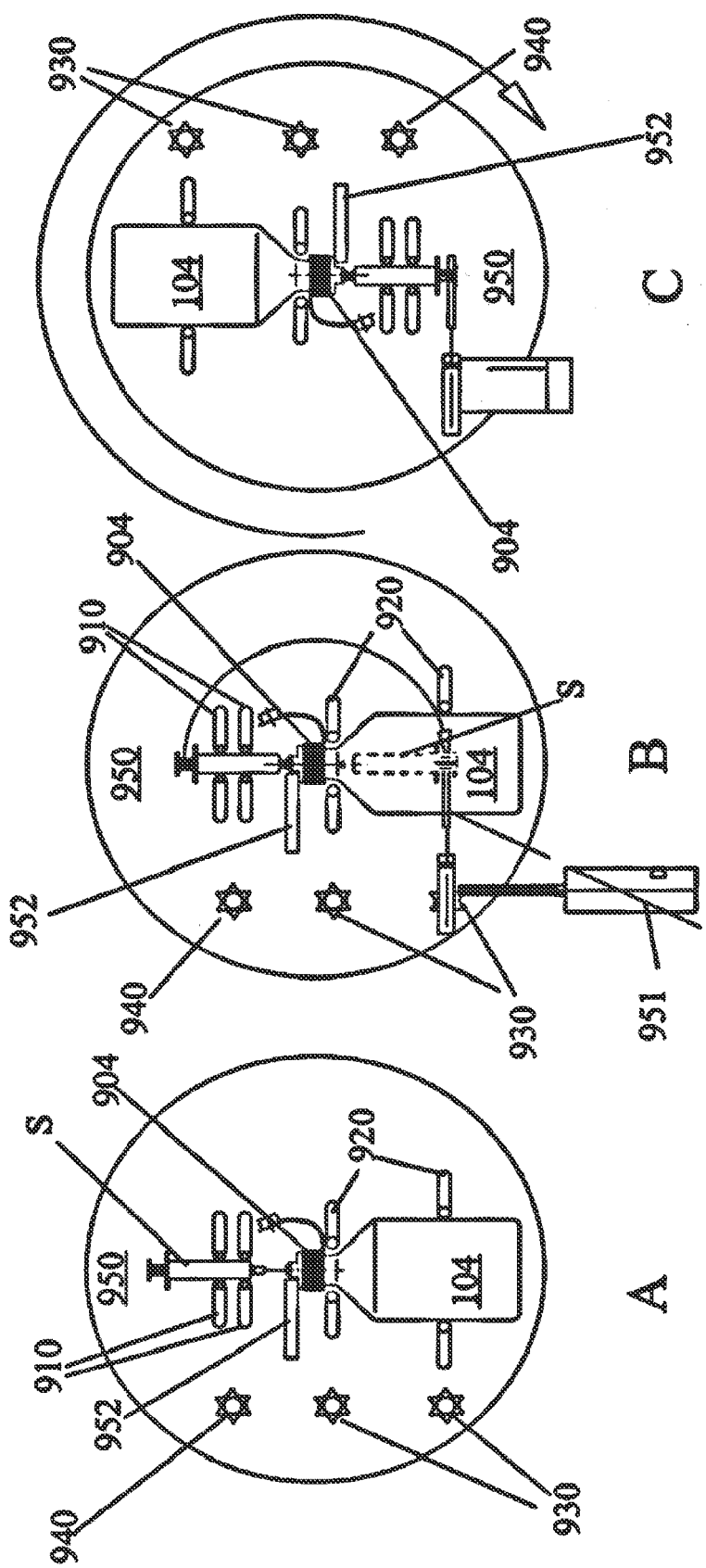
FIG. 18 is a perspective view of a simplified filling system with manually-adjustable medicine container grippers.

With additional reference to FIG. 18, the simplified syringe filling system utilizes a 180-degree rotating platform 950. It consists of two sets of manually adjustable "V" type grippers. One set of grippers 910 for the syringe and one set of grippers 920 for the bottle. The medicine bottle 104, equipped with the Baxa style cap is placed up against the stop block 952 and adjustable "V" grippers 920 are used to hold it in place. Once the bottle 104 and Baxa cap are placed up against the stop block 952, which is used as a reference locator for all containers with Baxa type caps, the syringe S is manually pushed into the Baxa Cap and is gripped via the upper set of syringe grippers 910. Both sets of grippers are operated both inward and outward with the aid of adjustment knobs 930, 940 and slots. Once engaged in the baxa cap, the platform 950 is rotated clockwise until the syringe plunger comes in contact with the spring loaded "V"s. These "V"s are operated by either servo motors (e.g., servo motor driven ball screw 951) or air cylinders. The later is for use with repeatable dosing in which the fill size is dictated by adjusting a stop for the air operated system to limit plunger travel. The former is operated in much the same fashion as the other syringe filling techniques previously described in the semi-automated descriptions except it consists of only a downward motion, thereby filling the syringe only. Syringe removal and releasing of the "V"s is performed manually.

Figure 19:
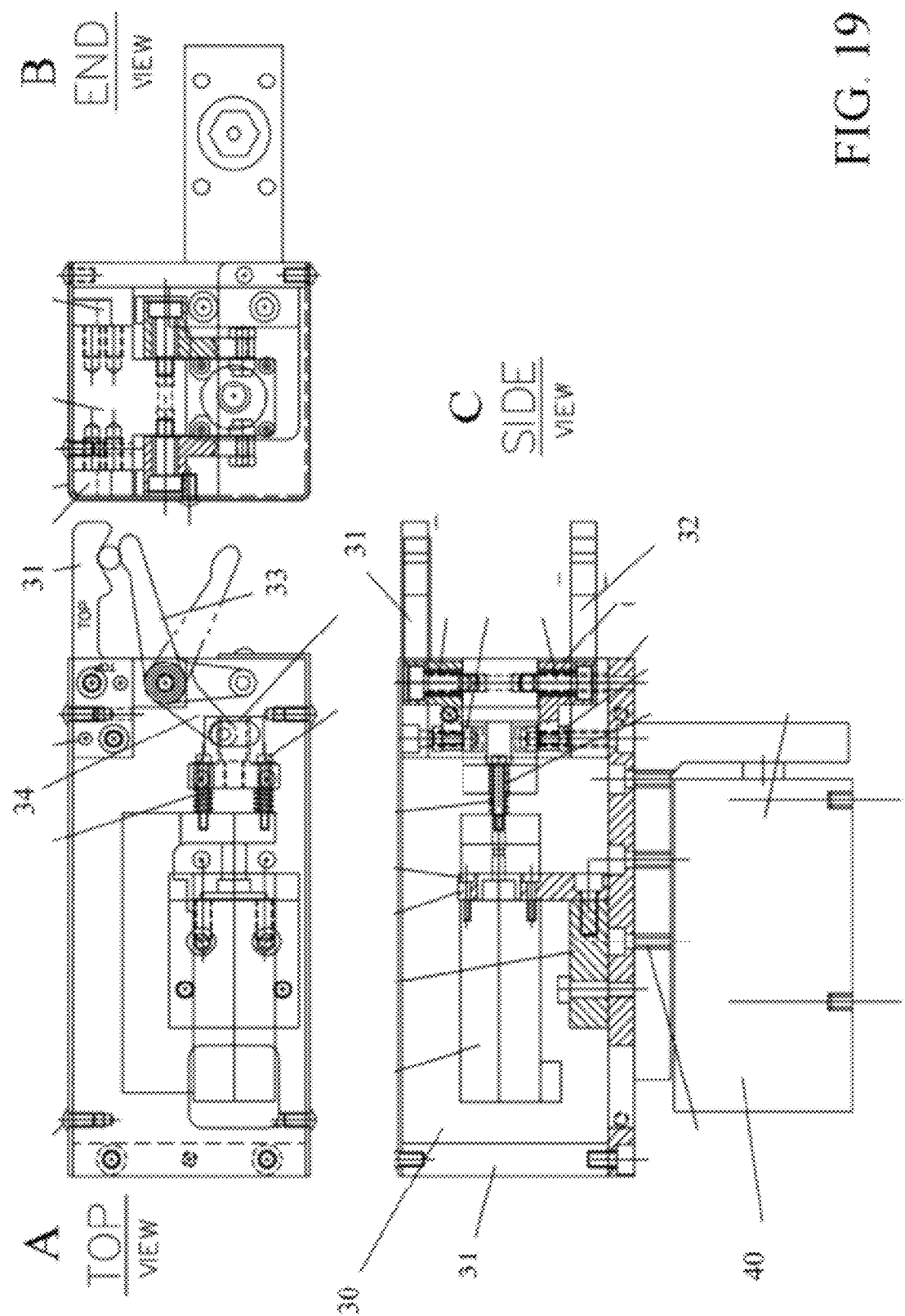
FIG. 19(A-C) shows a perspective, top cross-section and end cross-section, respectively, of a syringe in-feed pick and place mechanism that employs a carriage mounted grip arm apparatus

FIG. 20 is a flow diagram illustrating the method of use of the simplified embodiment, with previously-described steps being like-numbered. In use, at step 837 the operator manually selects the appropriate medicine container 104. The operator then scans the manufacturer barcode on medicine container 104 at the filling station to thereby confirm (via system database) that the correct medicine is being used. At step 839 the barcode on the syringe S is scanned to ensure correctness. If both are confirmed correct, then at step 840 the operator inserts medicine container 104 and syringe S as shown in FIG. 19. The gripper arms 910 and 920 are mounted on a servo-driven rotating turret 950. When both container 104 and syringe S are in position as seen at inset (A), the syringe S is automatically advanced such that its nozzle penetrates the elastomeric seal 225 as seen at inset (B). As seen at inset (C), the turret 950 rotates to invert the two. During rotation, the syringe S plunger moves into engagement with a fork shaped finger 120 that form a horizontally oriented "V" shaped opening as described previously in regard to FIG. 9. Fork shaped finger 120 yokes the plunger, and the plunger is automatically withdrawn via a servo or air cylinder 960 for calibrated fill of syringe S with medicine from container 104 (FIG. 20 step 845). Once filled, the turret 950 is reversed, the knobs 930, 940 loosened, and the syringe S and container 104 released.

The system minimizes downtime as well as processing time to take and fill orders, and is easy to clean and capable of maintaining an environment free from cross contamination. The system is open and accessible and allows interaction and oversight by a human operator at multiple points in the operation. Moreover, it is modular and permits a differing and upgradeable level of operator participation (from semi-automatic to and including full automation) based on the need of the individual institution.

It should now be apparent that the above-described system is driven by prescription orders in a just-in-time environment, manages all the various prescription containers containing the pharmaceuticals to be dispensed, as well as variously-sized oral syringes, to automatically converge them and orient, fill, label and cap each syringe and fully verify its work as it proceeds in order to avoid medication errors in the process. The pharmacy automation system for oral syringes substantially improves the pharmacist and technician productivity and maintains an environment free from cross contamination.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims and may be used with a variety of materials and components. This application is therefore intended to cover any variations, uses, or adaptations of the invention using its general principles. Further, this application is intended to cover such departures from the present disclosure as come within known or customary practice in the art to which this invention pertains.

We claim:

1. A method for semi-automated filling of oral syringes with medicines from a plurality of bulk medicine containers each bearing indicia inclusive of a first identifier and a type of medicine contained therein, said oral syringes being of various sizes and types all having a barrel, an annular flange encircling said barrel, a plunger slideably engaged in said barrel, and a flange at distal end of said plunger, and said plurality of bulk medicine containers being of various types, the method comprising the steps of:

maintaining a medicine database including manufacturer information on a plurality of medicine types;

inputting a plurality of medicine prescriptions for oral syringes, each of said plurality of medicine prescriptions including a type of medicine and dose size, to a queue of prescriptions to be fulfilled;

sorting said queue of medicine prescriptions by type of medicine;

fulfilling a batch subset of said inputted medicine prescriptions comprising all the same type of medicine, by the following substeps, automatically selecting a bulk medicine container of said type of medicine, manually retrieving said selected bulk medicine container, scanning said indicia on the retrieved bulk medicine container and comparing the type of medicine contained therein to the batch type of medicine to be fulfilled to confirm accurate manual retrieval, associating each inputted medicine prescription to be fulfilled with the retrieved bulk medicine container, automatically selecting an oral syringe size to fill with said retrieved bulk medicine container from among said plurality of syringe sizes based on capability to deliver the dose size of said inputted medicine prescription, generating a label bearing scan indicia inclusive of a unique syringe identifier, attaching said label to said selected oral syringe, manually loading said oral syringe and said selected bulk medicine container into a filling position in a loading station, and filling the loaded syringe with said type of medicine from said bulk medicine container by withdrawing a plunger of said syringe.

2. The method for semi-automated filling of oral syringes according to claim 1, further comprising a substep, after said substep of scanning said indicia on the retrieved bulk medicine container, of generating and attaching a second unique identifier to the retrieved bulk medicine container.

3. The method for semi-automated filling of oral syringes according to claim 1, further comprising a step of adapting said retrieved bulk medicine container for connection to an oral syringe nozzle by equipping said bulk medicine container with an adapter configured to permit connecting to oral syringe nozzles.

4. The method for semi-automated filling of oral syringes according to claim 1, wherein said substep of selecting said bulk medicine container of said type of medicine further comprises verifying that said bulk medicine container contains enough of said type of medicine.

5. The method for semi-automated tilling of oral syringes according to claim 2, further comprising a substep, after said substep of generating and attaching a second unique identifier to the retrieved bulk medicine container, of entering supplemental information relevant to the to the retrieved bulk medicine container into said medication database in association with said second unique identifier.

6. The method for semi-automated filling of oral syringes according to claim 3, wherein said step of adapting said retrieved bulk medicine container for connecting oral syringe nozzles comprises equipping said bulk medicine container with an adapter configured with a valve.

7. The method for semi-automated filling of oral syringes according to claim 1, wherein said step of fulfilling a batch subset of said inputted medicine prescriptions comprises, after each substep, a track-trace-and-validation substep to verify and compile an audit log for all of said substeps.

8. The method for semi-automated filling of oral syringes according to claim 1, further comprising, an initial step of logging a plurality of bulk medicine containers by the substeps of,
- adapting a plurality of bulk medicine containers for connection to an oral syringe nozzle by equipping said bulk medicine containers with an adapter configured to permit connecting of oral syringe nozzles,
- scanning the indicia on said plurality of bulk medicine containers to obtain said first identifier and t e of medicine contained therein, and
- generating and attaching a second unique identifier to said plurality of bulk medicine containers, and recording said second unique identifier in said medication database;
- entering supplemental information relevant to said plurality of bulk medicine containers into said medication database in association with said second unique identifier.

9. The method for semi-automated filling of oral syringes according to claim 1, further comprising a step of automatically shaking said filling station to thereby shake said bulk medicine container.

10. The method for semi-automated filling of oral syringes according to claim 1, further comprising a step of manually loading said oral syringe into a syringe loading station and indexing said oral syringe to a filling position by revolving said syringe.

11. The method for semi-automated filling of oral syringes according to claim 1, wherein said step of withdrawing the plunger of said syringe to fill said syringe with medicine is automatically accomplished with a servo-controlled arm for manipulating said plunger.

12. The method for semi-automated filling of oral syringes according to claim 11, wherein said step of withdrawing the plunger of said syringe to fill said syringe with medicine is automatically accomplished with a plurality of independent servo-controlled arms including at least a first arm and second arm both terminating in a forked end for engaging the syringe above and below a flange at distal end of said plunger, each said servo-controlled arm being independently servo-controlled and articulating along two axes.

* * * * *

UNITED STATES PATENT AND TRADEMARK OFFICE
CERTIFICATE OF CORRECTION

PATENT NO. : 9,033,006 B2  
APPLICATION NO. : 13/236577  
DATED : May 19, 2015  
INVENTOR(S) : Nicholas J. Perazzo et al.

It is certified that error appears in the above-identified patent and that said Letters Patent is hereby corrected as shown below:

IN THE CLAIMS

COLUMN 29 - Claim 8

Line 18, after the wording "and" remove the letters "t e" and replace by the wording "type" to read:

- containers to obtain said first identifier and type of medi-

Signed and Sealed this  
Third Day of November, 2015

Michelle K. Lee  
*Director of the United States Patent and Trademark Office*